(12) United States Patent
Rabiner et al.

(10) Patent No.: US 8,574,233 B2
(45) Date of Patent: *Nov. 5, 2013

(54) PHOTODYNAMIC BONE STABILIZATION SYSTEMS AND METHODS FOR REINFORCING BONE

(75) Inventors: Robert A. Rabiner, Tiverton, RI (US); Dennis P. Colleran, Mansfield, MA (US); Anthony W. O'Leary, Walpole, MA (US); Narissa Y. Chang, Mansfield, MA (US); Douglas A. Kornbluth, Foxboro, MA (US); Justin G. Dye, Mansfield, MA (US); Joshua M. Morin, Newington, CT (US)

(73) Assignee: IlluminOss Medical, Inc., East Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/616,416

(22) Filed: Sep. 14, 2012

(65) Prior Publication Data
US 2013/0023877 A1    Jan. 24, 2013

Related U.S. Application Data

(63) Continuation of application No. 12/755,784, filed on Apr. 7, 2010.

(60) Provisional application No. 61/167,276, filed on Apr. 7, 2009.

(51) Int. Cl.
*A61B 17/72*    (2006.01)

(52) U.S. Cl.
USPC .................. 606/63; 606/62; 606/92; 606/262

(58) Field of Classification Search
USPC .................. 606/92–95, 62–63, 262
See application file for complete search history.

(56) References Cited

U.S. PATENT DOCUMENTS

| 4,280,233 A | 7/1981 | Raab |
| 4,294,251 A | 10/1981 | Greenwald et al. |

(Continued)

FOREIGN PATENT DOCUMENTS

| DE | 40 28 466 | 3/1992 |
| EP | 0 709 698 | 5/1996 |

(Continued)

OTHER PUBLICATIONS

Jovanovic et al., "Fixion Nails for Humeral Fractures, Injury", Int. J. Care Injured, vol. 35, Issue 11, pp. 1140-1142, Nov. 2004.

(Continued)

*Primary Examiner* — Eduardo C Robert
*Assistant Examiner* — Julianna N Harvey
(74) *Attorney, Agent, or Firm* — Greenberg Traurig, LLP; David J. Dykeman; Danielle T. Abramson

(57) ABSTRACT

Photodynamic bone stabilization systems are disclosed herein. In an embodiment, a photodynamic bone stabilization system includes a catheter having an elongated shaft with a proximal end adapter, a distal end releasably engaging an expandable portion, and a longitudinal axis therebetween; a light-conducting fiber configured to transmit light energy to the expandable portion; a light-sensitive liquid monomer comprising an initiator, wherein the initiator is activated when the light-conducting fiber transmits the light energy to initiate polymerization of the light-sensitive liquid monomer; and a cooling medium configured to control polymerization temperature, wherein the catheter comprises an inner void sufficiently designed to pass the light-sensitive liquid monomer into the expandable portion, and wherein the catheter comprises an inner lumen sufficiently designed to pass the light-conducting fiber into the expandable portion and configured to circulate the cooling medium.

20 Claims, 12 Drawing Sheets

(56) References Cited

U.S. PATENT DOCUMENTS

| | | | |
|---|---|---|---|
| 4,313,434 A | 2/1982 | Segal | |
| 4,341,691 A | 7/1982 | Anuta | |
| 4,369,772 A | 1/1983 | Miller | |
| 4,414,608 A | 11/1983 | Furihata | |
| 4,422,719 A | 12/1983 | Orcutt | |
| 4,433,898 A | 2/1984 | Nasiri | |
| 4,462,394 A | 7/1984 | Jacobs | |
| 4,466,435 A | 8/1984 | Murray | |
| 4,562,598 A | 1/1986 | Kranz | |
| 4,686,973 A | 8/1987 | Frisch | |
| 4,697,584 A | 10/1987 | Haynes | |
| 4,735,625 A | 4/1988 | Davidson | |
| 4,870,953 A | 10/1989 | DonMicheal et al. | |
| 4,888,024 A | 12/1989 | Powlan | |
| 4,904,391 A | 2/1990 | Freeman | |
| 4,961,424 A | 10/1990 | Kubota et al. | |
| 4,963,151 A | 10/1990 | Ducheyne et al. | |
| 4,969,888 A | 11/1990 | Scholten et al. | |
| 5,030,093 A | 7/1991 | Mitnick | |
| 5,049,157 A | 9/1991 | Mittelmeier et al. | |
| 5,085,660 A | 2/1992 | Lin | |
| 5,092,899 A | 3/1992 | Forte | |
| 5,102,413 A | 4/1992 | Poddar | |
| 5,108,404 A | 4/1992 | Scholten et al. | |
| 5,112,333 A | 5/1992 | Fixel | |
| 5,295,733 A | 3/1994 | LeBegue | |
| 5,295,962 A | 3/1994 | Crocker et al. | |
| 5,303,718 A | 4/1994 | Krajicek | |
| 5,316,550 A | 5/1994 | Forte | |
| 5,336,699 A | 8/1994 | Cooke et al. | |
| 5,372,598 A | 12/1994 | Luhr et al. | |
| 5,391,144 A | 2/1995 | Sakurai et al. | |
| 5,415,654 A | 5/1995 | Daikuzono | |
| 5,423,850 A | 6/1995 | Berger | |
| 5,432,876 A | 7/1995 | Appeldorn et al. | |
| 5,443,468 A | 8/1995 | Johnson | |
| 5,462,552 A | 10/1995 | Kiester | |
| 5,480,400 A | 1/1996 | Berger | |
| 5,538,514 A | 7/1996 | Hawkins | |
| 5,548,676 A | 8/1996 | Savage, Jr. | |
| 5,554,111 A | 9/1996 | Morrey et al. | |
| 5,556,429 A | 9/1996 | Felt | |
| 5,571,204 A | 11/1996 | Nies | |
| 5,658,310 A | 8/1997 | Berger | |
| 5,658,963 A | 8/1997 | Qian et al. | |
| 5,705,181 A | 1/1998 | Cooper et al. | |
| 5,707,374 A | 1/1998 | Schmidt | |
| 5,713,901 A | 2/1998 | Tock | |
| 5,795,353 A | 8/1998 | Felt | |
| 5,824,087 A | 10/1998 | Aspden et al. | |
| 5,827,289 A | 10/1998 | Reiley et al. | |
| 5,888,220 A | 3/1999 | Felt et al. | |
| 5,897,557 A | 4/1999 | Chin et al. | |
| 5,908,433 A | 6/1999 | Eager et al. | |
| 5,972,015 A | 10/1999 | Scribner et al. | |
| 5,980,075 A | 11/1999 | Sheaffer | |
| 5,980,253 A | 11/1999 | Oxman et al. | |
| 5,987,199 A | 11/1999 | Zarian et al. | |
| 5,989,230 A | 11/1999 | Frassica | |
| 6,008,264 A | 12/1999 | Ostler et al. | |
| 6,019,761 A | 2/2000 | Gustilo | |
| 6,019,774 A | 2/2000 | Weiss et al. | |
| 6,033,411 A | 3/2000 | Preissman | |
| 6,039,762 A | 3/2000 | McKay | |
| 6,042,380 A | 3/2000 | De Rowe | |
| 6,048,346 A | 4/2000 | Reiley et al. | |
| 6,059,789 A | 5/2000 | Dinger et al. | |
| 6,066,154 A * | 5/2000 | Reiley et al. | 606/192 |
| 6,079,868 A | 6/2000 | Rydell | |
| 6,103,203 A | 8/2000 | Fischer | |
| 6,110,176 A | 8/2000 | Shapira | |
| 6,121,341 A | 9/2000 | Sawhney et al. | |
| 6,127,597 A | 10/2000 | Beyar et al. | |
| 6,140,452 A | 10/2000 | Felt et al. | |
| 6,159,236 A | 12/2000 | Biel | |
| 6,179,852 B1 | 1/2001 | Strickland et al. | |
| 6,195,477 B1 | 2/2001 | Denuto et al. | |
| 6,200,134 B1 | 3/2001 | Kovac et al. | |
| 6,217,581 B1 | 4/2001 | Tolson | |
| 6,223,085 B1 * | 4/2001 | Dann et al. | 607/101 |
| 6,224,630 B1 | 5/2001 | Bao et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,248,131 B1 | 6/2001 | Felt et al. | |
| 6,258,089 B1 | 7/2001 | Campbell et al. | |
| 6,261,289 B1 | 7/2001 | Levy | |
| 6,280,456 B1 | 8/2001 | Scribner et al. | |
| 6,282,013 B1 | 8/2001 | Ostler et al. | |
| 6,290,382 B1 | 9/2001 | Bourn et al. | |
| 6,299,597 B1 | 10/2001 | Buscemi et al. | |
| 6,306,177 B1 | 10/2001 | Felt et al. | |
| 6,319,255 B1 | 11/2001 | Grundei et al. | |
| 6,332,894 B1 | 12/2001 | Stalcup et al. | |
| 6,336,914 B1 | 1/2002 | Gillespie, III | |
| 6,336,930 B1 | 1/2002 | Stalcup et al. | |
| 6,358,252 B1 | 3/2002 | Shapira | |
| 6,387,098 B1 | 5/2002 | Cole et al. | |
| 6,395,007 B1 | 5/2002 | Bhatnagar et al. | |
| 6,416,531 B2 | 7/2002 | Chen | |
| 6,416,737 B1 | 7/2002 | Manolagas et al. | |
| 6,419,483 B1 | 7/2002 | Adam et al. | |
| 6,423,083 B2 | 7/2002 | Reiley et al. | |
| 6,425,923 B1 * | 7/2002 | Stalcup et al. | 623/23.58 |
| 6,440,444 B2 | 8/2002 | Boyce et al. | |
| 6,443,988 B2 | 9/2002 | Felt et al. | |
| 6,447,514 B1 | 9/2002 | Stalcup et al. | |
| 6,458,375 B1 | 10/2002 | Gertzman et al. | |
| 6,478,751 B1 | 11/2002 | Krueger et al. | |
| 6,485,512 B1 | 11/2002 | Cheng | |
| 6,494,883 B1 | 12/2002 | Ferree | |
| 6,524,251 B2 | 2/2003 | Rabiner et al. | |
| 6,524,313 B1 | 2/2003 | Fassier et al. | |
| 6,551,321 B1 | 4/2003 | Burkinshaw et al. | |
| 6,551,337 B1 | 4/2003 | Rabiner et al. | |
| 6,565,528 B1 | 5/2003 | Mueller | |
| 6,579,277 B1 | 6/2003 | Rabiner et al. | |
| 6,579,279 B1 | 6/2003 | Rabiner et al. | |
| 6,620,185 B1 | 9/2003 | Harvie et al. | |
| 6,623,505 B2 | 9/2003 | Scribner et al. | |
| 6,632,235 B2 | 10/2003 | Weikel et al. | |
| 6,648,881 B2 | 11/2003 | KenKnight et al. | |
| 6,652,547 B2 | 11/2003 | Rabiner et al. | |
| 6,652,587 B2 | 11/2003 | Felt et al. | |
| 6,660,013 B2 | 12/2003 | Rabiner et al. | |
| 6,679,873 B2 | 1/2004 | Rabiner et al. | |
| 6,695,781 B2 | 2/2004 | Rabiner et al. | |
| 6,695,782 B2 | 2/2004 | Rabiner et al. | |
| 6,696,073 B2 | 2/2004 | Boyce et al. | |
| 6,716,216 B1 | 4/2004 | Boucher et al. | |
| 6,719,773 B1 | 4/2004 | Boucher et al. | |
| 6,726,691 B2 * | 4/2004 | Osorio et al. | 606/94 |
| 6,730,048 B1 | 5/2004 | Hare et al. | |
| 6,733,451 B2 | 5/2004 | Rabiner et al. | |
| 6,733,513 B2 | 5/2004 | Boyle et al. | |
| 6,740,093 B2 | 5/2004 | Hochschuler et al. | |
| 6,755,862 B2 | 6/2004 | Keynan | |
| 6,783,530 B1 | 8/2004 | Levy | |
| 6,802,835 B2 | 10/2004 | Rabiner et al. | |
| 6,818,018 B1 | 11/2004 | Sawhney | |
| 6,852,095 B1 | 2/2005 | Ray | |
| 6,866,678 B2 | 3/2005 | Shenderova et al. | |
| 6,869,442 B2 | 3/2005 | Cheng | |
| 6,875,212 B2 | 4/2005 | Shaolian et al. | |
| 6,885,246 B2 | 4/2005 | Tsutsui et al. | |
| 6,887,246 B2 | 5/2005 | Bhatnagar et al. | |
| 6,887,275 B2 | 5/2005 | Carchidi et al. | |
| 6,899,713 B2 | 5/2005 | Shaolian et al. | |
| 6,899,719 B2 | 5/2005 | Reiley et al. | |
| 6,932,843 B2 | 8/2005 | Smith et al. | |
| 6,964,667 B2 | 11/2005 | Shaolian et al. | |
| 6,979,341 B2 | 12/2005 | Scribner et al. | |
| 6,981,981 B2 | 1/2006 | Reiley et al. | |
| 7,001,431 B2 | 2/2006 | Bao et al. | |

| | | |
|---|---|---|
| 7,008,433 B2 | 3/2006 | Voellmicke et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,547,319 B2 | 6/2009 | Segal et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim |
| 8,210,729 B2 | 7/2012 | O'Leary et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,512,338 B2 | 8/2013 | Rabiner et al. |
| 2001/0011174 A1 | 8/2001 | Reiley et al. |
| 2001/0044626 A1 | 11/2001 | Reiley et al. |
| 2002/0156482 A1 | 10/2002 | Scribner et al. |
| 2002/0161373 A1 | 10/2002 | Osorio et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2005/0010231 A1 | 1/2005 | Myers |
| 2005/0015140 A1 | 1/2005 | deBeer |
| 2005/0015148 A1 | 1/2005 | Jansen et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1* | 4/2005 | Studer ................ 623/17.12 |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1* | 6/2006 | Truckai et al. ................ 606/94 |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osario et al. |
| 2007/0255287 A1 | 11/2007 | Rabiner |
| 2008/0015500 A1 | 1/2008 | Herweck et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154368 A1 | 6/2008 | Justis et al. |
| 2008/0154373 A1 | 6/2008 | Protopsaltis et al. |
| 2008/0183122 A1 | 7/2008 | Fisher et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburner et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0093887 A1 | 4/2009 | Walter et al. |
| 2009/0112196 A1 | 4/2009 | Rabiner et al. |
| 2009/0171265 A1 | 7/2009 | Doty et al. |
| 2009/0171358 A1 | 7/2009 | Chang et al. |

| | | | |
|---|---|---|---|
| 2009/0177204 A1 | 7/2009 | Colleran et al. | |
| 2009/0182336 A1 | 7/2009 | Brenzel et al. | |
| 2009/0187192 A1 | 7/2009 | Rabiner et al. | |
| 2009/0216232 A1 | 8/2009 | Buford, III et al. | |
| 2009/0228007 A1 | 9/2009 | Justin et al. | |
| 2009/0254064 A1 | 10/2009 | Boatman | |
| 2009/0287309 A1 | 11/2009 | Walch et al. | |
| 2010/0234958 A1 | 9/2010 | Linares | |
| 2010/0249942 A1 | 9/2010 | Goswami et al. | |
| 2010/0256641 A1 | 10/2010 | Rabiner et al. | |
| 2010/0262069 A1 | 10/2010 | Rabiner et al. | |
| 2010/0262188 A1 | 10/2010 | Rabiner et al. | |
| 2010/0265733 A1 | 10/2010 | O'Leary et al. | |
| 2010/0318087 A1 | 12/2010 | Scribner et al. | |
| 2010/0331850 A1 | 12/2010 | Rabiner | |
| 2011/0004213 A1 | 1/2011 | Rabiner et al. | |
| 2011/0009871 A1 | 1/2011 | Rabiner | |
| 2011/0029093 A1 | 2/2011 | Bojarski et al. | |
| 2011/0046746 A1 | 2/2011 | Rabiner et al. | |
| 2011/0098713 A1 | 4/2011 | Rabiner et al. | |
| 2011/0110114 A1 | 5/2011 | Papac et al. | |
| 2011/0118740 A1 | 5/2011 | Rabiner et al. | |
| 2011/0160870 A1 | 6/2011 | Baumgartner et al. | |
| 2011/0166306 A1 | 7/2011 | Stansbury et al. | |
| 2011/0313356 A1 | 12/2011 | Rabiner et al. | |
| 2012/0165941 A1 | 6/2012 | Rabiner et al. | |
| 2012/0262939 A1 | 10/2012 | O'Leary et al. | |
| 2012/0289968 A1 | 11/2012 | Rabiner | |
| 2013/0003406 A1 | 1/2013 | O'Leary et al. | |
| 2013/0006304 A1 | 1/2013 | Rabiner et al. | |
| 2013/0013008 A1 | 1/2013 | Rabiner et al. | |
| 2013/0013009 A1 | 1/2013 | Colleran et al. | |
| 2013/0013010 A1 | 1/2013 | Rabiner et al. | |
| 2013/0023876 A1 | 1/2013 | Rabiner et al. | |
| 2013/0023886 A1 | 1/2013 | Rabiner et al. | |
| 2013/0041472 A1 | 2/2013 | Rabiner et al. | |
| 2013/0046390 A1 | 2/2013 | Rabiner et al. | |
| 2013/0066326 A1 | 3/2013 | Rabiner et al. | |
| 2013/0158607 A1 | 6/2013 | Rabiner et al. | |
| 2013/0184715 A1 | 7/2013 | Rabiner et al. | |

FOREIGN PATENT DOCUMENTS

| | | |
|---|---|---|
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2007/059259 | 5/2007 |
| WO | WO 2007/127255 | 11/2007 |
| WO | WO 2007/127260 | 11/2007 |
| WO | WO 2008/063265 | 5/2008 |
| WO | WO 2009/059090 | 5/2009 |
| WO | WO 2009/082688 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO2013/059609 | 4/2013 |

OTHER PUBLICATIONS

Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.

Waris et al., "Bioabsorbable Miniplating Versus Metallic Fixation for Metacarpal Fractures", Clinical Orthopaedics and Related Research, No. 410, pp. 310-319, May 2003.

Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.

PCT International Search Report based on PCT/US07/20402 dated Apr. 1, 2008.

PCT International Search Report based on PCT/US07/10050 dated Apr. 17, 2008.

PCT International Search Report based on PCT/US07/10038 dated Aug. 27, 2008.

PCT International Search Report based on PCT/US08/81929 dated Jan. 12, 2009.

PCT International Search Report based on PCT/US08/81924 dated Feb. 9, 2009.

PCT International Search Report based on PCT/US08/87630 dated Feb. 24, 2009.

PCT International Search Report based on PCT/US10/30275 dated Aug. 11, 2010.

PCT International Search Report based on PCT/US10/56219 dated Jan. 20, 2011.

PCT International Search Report based on PCT/US10/46003 dated May 24, 2011.

PCT International Search Report based on PCT/US11/38389 dated Sep. 22, 2011.

PCT International Search Report based on PCT/US11/66871 dated May 1, 2012.

USPTO Office Action in U.S. Appl. No. 11/789,906 mailed Apr. 29, 2009.

USPTO Office Action in U.S. Appl. No. 11/789,906 mailed Mar. 11, 2010.

USPTO Office Action in U.S. Appl. No. 11/789,906 mailed Apr. 30, 2010.

USPTO Office Action in U.S. Appl. No. 11/789,907 mailed May 11, 2010.

USPTO Office Action in U.S. Appl. No. 11/903,123 mailed Jul. 1, 2010.

USPTO Office Action in U.S. Appl. No. 11/964,370 mailed Dec. 9, 2010.

USPTO Office Action in U.S. Appl. No. 11/964,370 mailed Apr. 28, 2011.

USPTO Office Action in U.S. Appl. No. 11/964,370 mailed Sep. 23, 2011.

USPTO Office Action in U.S. Appl. No. 11/964,370 mailed Mar. 16, 2012.

USPTO Office Action in U.S. Appl. No. 12/262,411 mailed Sep. 1, 2010.

USPTO Office Action in U.S. Appl. No. 12/755,784 mailed Dec. 23, 2011.

USPTO Office Action in U.S. Appl. No. 12/756,014 mailed May 11, 2012.

USPTO Office Action in U.S. Appl. No. 12/858,924 mailed Oct. 24, 2011.

USPTO Office Action in U.S. Appl. No. 12/858,924 mailed Apr. 4, 2012.

USPTO Office Action in U.S. Appl. No. 12/875,460 mailed Mar. 8, 2012.

USPTO Office Action in U.S. Appl. No. 12/886,288 mailed Dec. 27, 2011.

USPTO Office Action in U.S. Appl. No. 12/262,370 mailed May 29, 2012.

USPTO Office Action in U.S. Appl. No. 12/943,544 mailed Jun. 8, 2012.

(56) References Cited

OTHER PUBLICATIONS

USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/859,680 mailed Jan. 17, 2013.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/756,014 mailed Jan. 22, 2013.
USPTO Office Action in U.S. Appl. No. 13/088,916 mailed Jan. 23, 2013.
USPTO Office Action in U.S. Appl. No. 13/772,947 mailed Jun. 19, 2013.
USPTO Office Action in U.S. Appl. No. 12/859,680 mailed Jul. 9, 2013.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/088,916 mailed May 13, 2013.

* cited by examiner

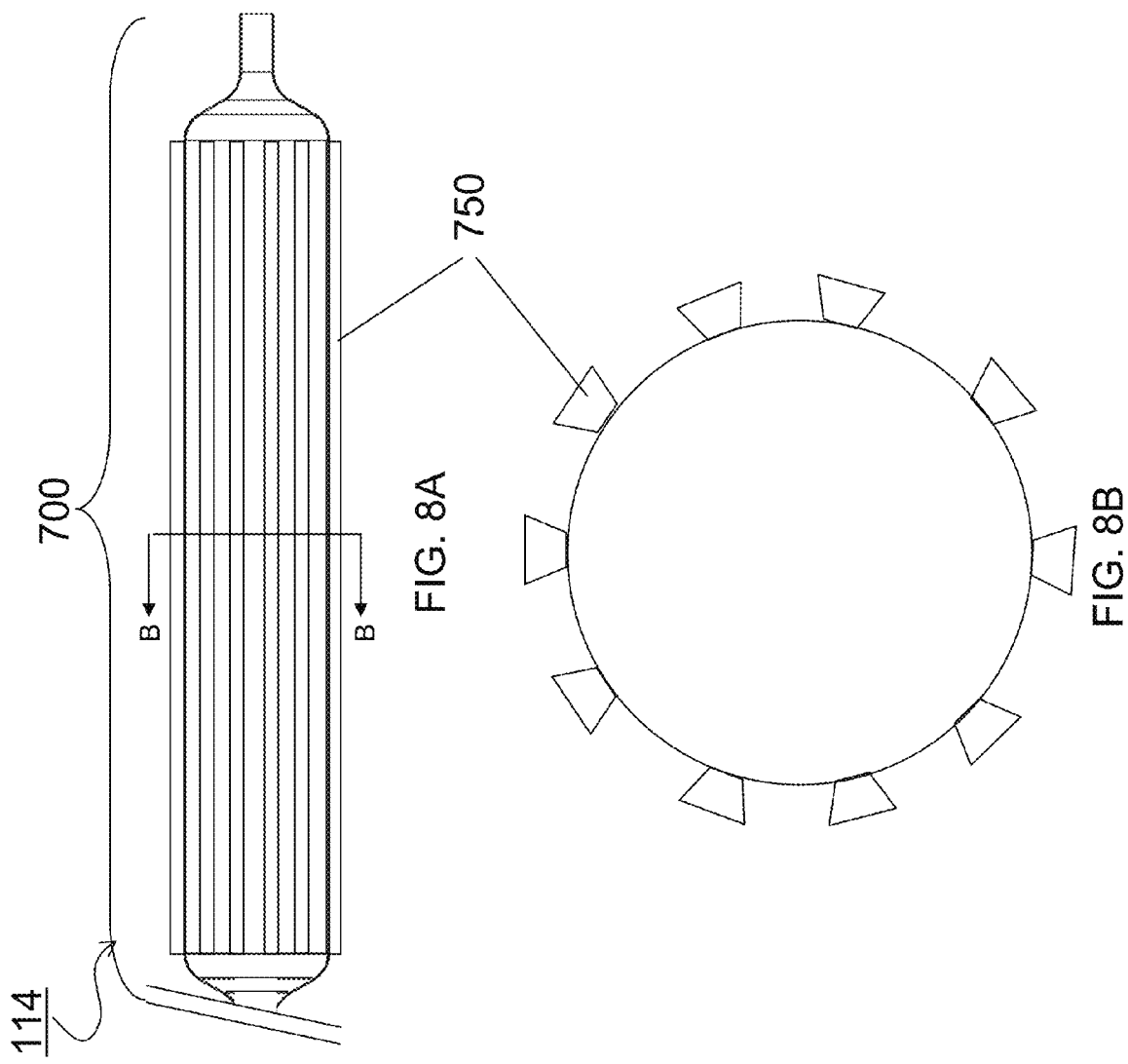

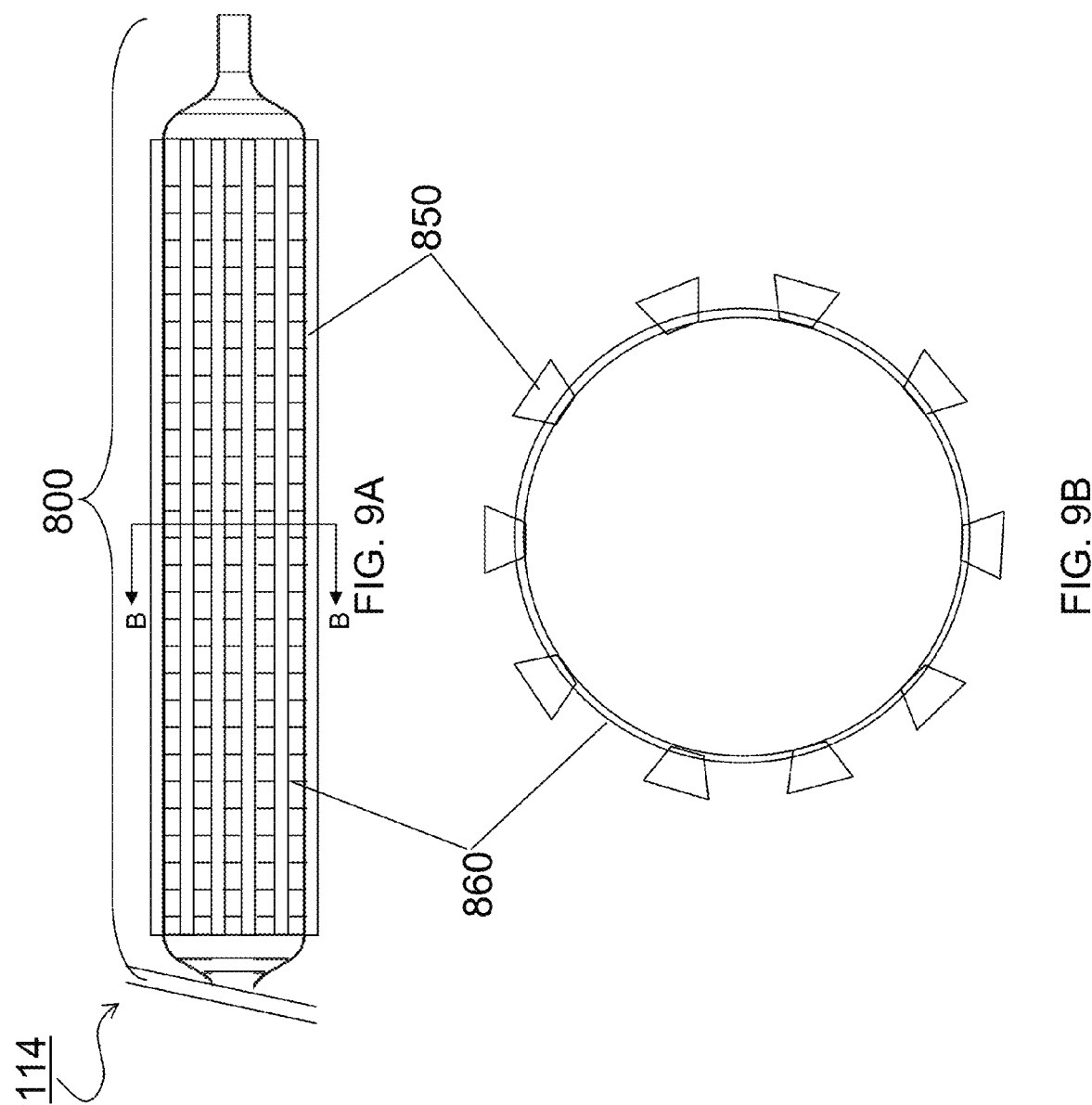

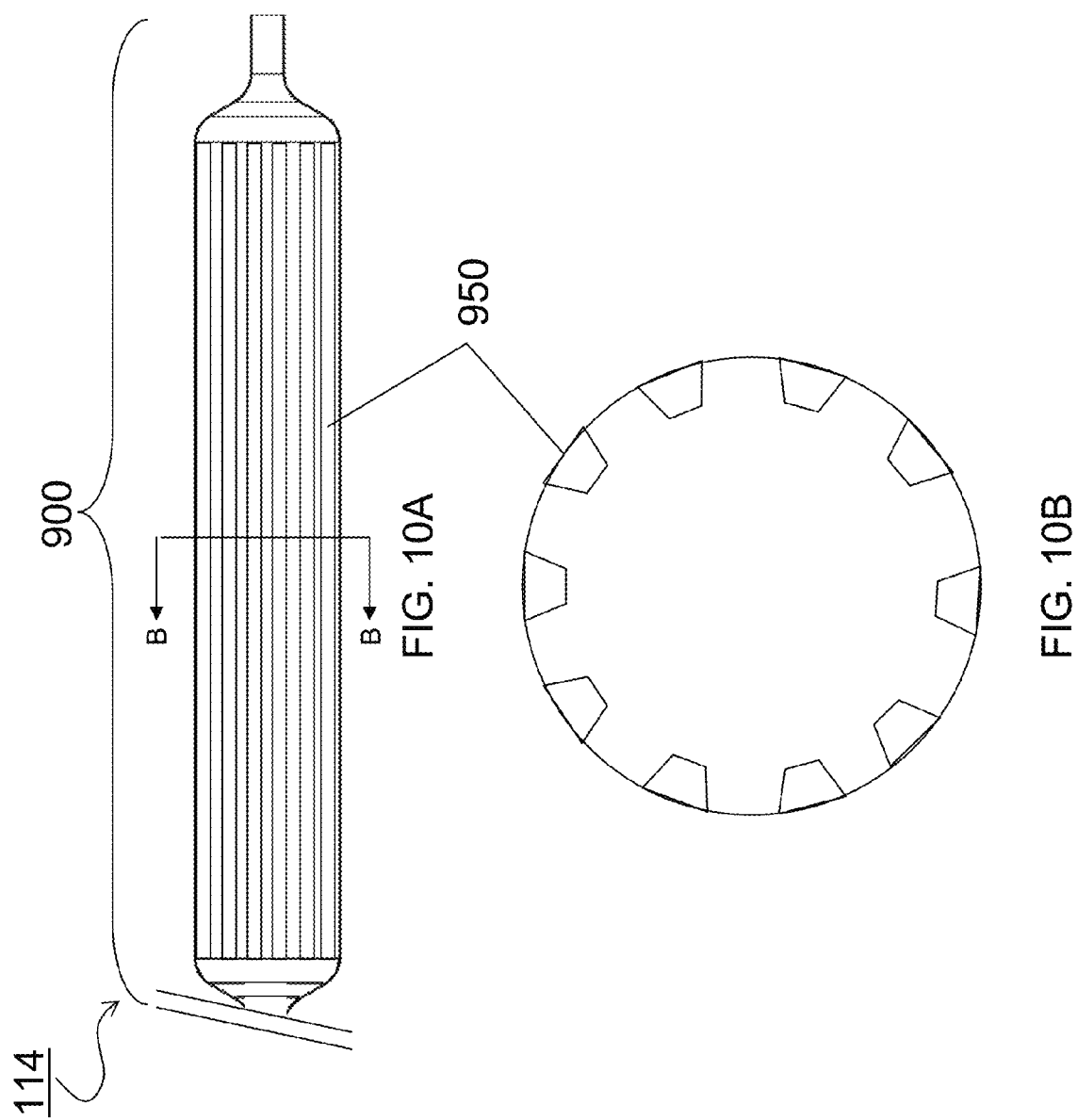

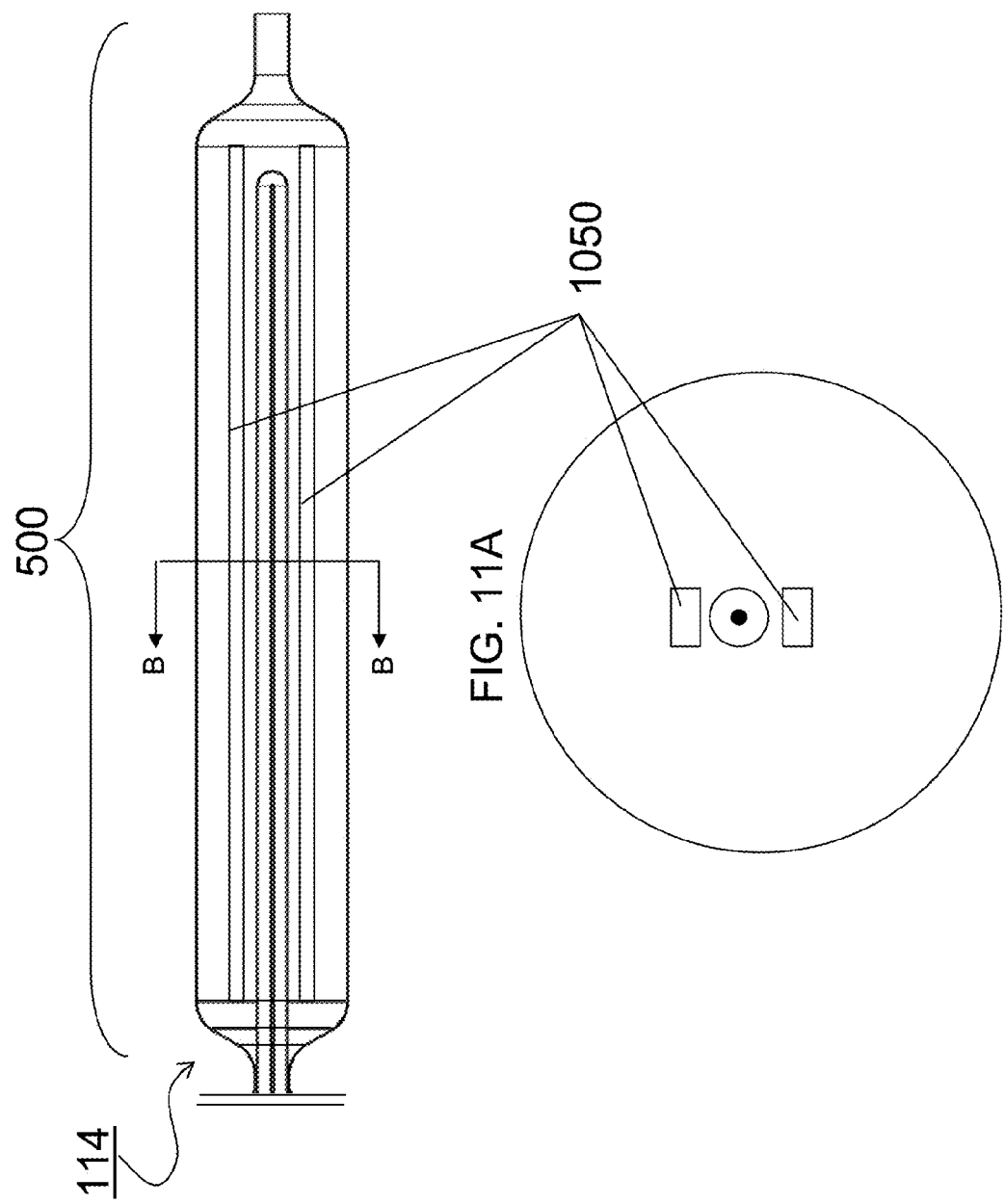

PHOTODYNAMIC BONE STABILIZATION SYSTEMS AND METHODS FOR REINFORCING BONE

RELATED APPLICATIONS

This application is a continuation of U.S. patent application Ser. No. 12/755,784, filed on Apr. 7, 2010, which claims priority to and the benefit of U.S. Provisional Patent Application No. 61/167,276, filed on Apr. 7, 2009, the entireties of all these applications are hereby incorporated herein by reference.

FIELD

The embodiments disclosed herein relate to minimally invasive orthopedic procedures, and more particularly to photodynamic bone stabilization systems for use in repairing a weakened or fractured bone.

BACKGROUND

Bone fracture repairs are surgical procedures to realign and stabilize broken bones, and are conventionally carried out using plates, nails, screws or pins. Current methods of treating bone fractures each have significant drawbacks. For example, tendon adhesions are typical in casting; soft tissue injury occurs frequently when plates or screws are inserted during open surgery; and K-wires do not provide sufficient support for immediate movement. Frequently, these procedures require extensive post operative recuperation and present with co-morbidities, such as, stiffness and loss of range of motion. For example, post surgical soft tissue injury can reduce mobility, and callous may incorporate into surrounding tendons further reducing mobility.

SUMMARY

Photodynamic bone stabilization systems are disclosed herein. According to aspects illustrated herein, a photodynamic bone stabilization system includes a catheter having an elongated shaft with a proximal end adapter, a distal end releasably engaging an expandable portion, and a longitudinal axis therebetween; a light-conducting fiber configured to transmit light energy to the expandable portion; a light-sensitive liquid monomer comprising an initiator, wherein the initiator is activated when the light-conducting fiber transmits the light energy to initiate polymerization of the light-sensitive liquid monomer; and a cooling medium configured to control polymerization temperature, wherein the catheter comprises an inner void sufficiently designed to pass the light-sensitive liquid monomer into the expandable portion, and wherein the catheter comprises an inner lumen sufficiently designed to pass the light-conducting fiber into the expandable portion and configured to circulate the cooling medium.

According to aspects illustrated herein, a photodynamic bone stabilization system includes a light-conducting fiber configured to transmit light energy; a light-sensitive liquid monomer comprising an initiator, wherein the initiator is activated when the light-conducting fiber transmits the light energy; a pressurizing medium configured to control polymerization shrinkage; and a catheter having an elongated shaft with a proximal end adapter, a distal end releasably engaging an expandable portion, and a longitudinal axis therebetween, wherein the catheter comprises an inner void and an inner lumen, wherein the inner void is sufficiently designed to pass the light-sensitive liquid monomer into the expandable portion, wherein the inner lumen is sufficiently designed to pass the light-conducting fiber into the expandable portion, and wherein the inner lumen comprises expandable portions configured to expand when the pressurizing medium is delivered to the inner lumen so as to cause internal diameter pressure against the light-sensitive liquid monomer contained within the expandable portion during polymerization.

According to aspects illustrated herein, a method includes providing a system comprising a catheter having an elongated shaft with a proximal end adapter, a distal end releasably engaging an expandable portion, and a longitudinal axis therebetween; a light-conducting fiber configured to transmit light energy to the expandable portion; a light-sensitive liquid monomer comprising an initiator, wherein the initiator is activated when the light-conducting fiber transmits the light energy, to initiate polymerization of the light-sensitive liquid monomer; and a cooling medium configured to control polymerization temperature, wherein the catheter comprises an inner void sufficiently designed to pass the light-sensitive liquid monomer into the expandable portion, and wherein the catheter comprises an inner lumen sufficiently designed to pass the light-conducting fiber into the expandable portion and configured to circulate the cooling medium; inserting the expandable portion of the system into an intramedullary canal spanning a fracture site comprising a plurality of fractured pieces; infusing the light-sensitive liquid monomer into the inner void of the catheter so that the light-sensitive liquid monomer expands the expandable portion until the fractured pieces are substantially restored to their natural positions; inserting the light-conducting fiber into the inner lumen of the catheter so that the light-conducting fiber resides in the expandable portion; activating the light-conducting fiber to transmit light energy to the expandable portion to initiate in situ polymerization of the light-sensitive liquid monomer within the expandable portion; infusing the cooling medium into the inner lumen of the catheter to control polymerization temperature; and completing the in situ polymerization of the light-sensitive liquid monomer to harden the expandable portion at the fracture site.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 5A is a side view of an embodiment of a distal end of a photodynamic bone stabilization system for repairing a weakened or fractured bone positioned within a fractured bone. The distal end includes an expandable portion having an internal lumen penetrating through a distal end of the expandable portion for cooling through the length of the expandable portion. The distal end of the expandable portion releaseably engages a catheter. FIG. 5B is a side view of the expandable portion of FIG. 5A after a light-sensitive liquid monomer has been added to the expandable portion, causing the expandable portion to inflate. FIG. 5C is a side view of the expandable portion of FIG. 5A after a light-conducting fiber has been inserted into the expandable portion to transmit energy to initiate a curing process. FIG. 5D is a side view of the hardened expandable portion of FIG. 5A positioned within the weakened or fractured bone after the catheter has been released.

FIG. 8A shows a side view of an embodiment of a distal end of a photodynamic bone stabilization system for repairing a weakened or fractured bone according to the present disclosure. The distal end includes an expandable portion (illustrated in an expanded position) having external stiffening members.

FIG. 8B shows a sectional view of the expandable portion of FIG. 8A taken along line B-B.

FIG. 9A shows a side view of an embodiment of a distal end of a photodynamic bone stabilization system for repairing a weakened or fractured bone according to the present disclosure. The distal end includes an expandable portion (illustrated in an expanded position) having external stiffening members interconnected with one another via connecting means.

FIG. 9B shows a sectional view of the expandable portion of FIG. 9A taken along line B-B.

FIG. 10A shows a side view of an embodiment of a distal end of a photodynamic bone stabilization system for repairing a weakened or fractured bone according to the present disclosure. The distal end includes an expandable portion (illustrated in an expanded position) having internal stiffening members.

FIG. 10B shows a sectional view of the expandable portion of FIG. 10A taken along line B-B.

FIG. 11A shows a side view of an embodiment of a distal end of a photodynamic bone stabilization system for repairing a weakened or fractured bone according to the present disclosure. The distal end includes an expandable portion (illustrated in an expanded position) having internal stiffening members.

FIG. 11B shows a sectional view of the balloon portion of FIG. 11A taken along line B-B.

FIG. 12B shows a stiffening member having a rectangular cross-section. FIG. 12C shows a stiffening member having a trapezoid cross-section. FIG. 12D shows a stiffening member having a unique cross-section. FIG. 12E shows a stiffening member having a triangular cross-section. FIG. 12F shows a stiffening member having a bow-tie cross-section. FIG. 12G shows a stiffening member having a rounded rectangular cross-section.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The embodiments disclosed herein relate to minimally invasive orthopedic procedures, and more particularly to photodynamic bone stabilization systems for use in repairing a weakened or fractured bone. In an embodiment, a photodynamic bone stabilization system includes a thin-walled, non-compliant, expandable portion releasably mounted on a small diameter, flexible insertion catheter. In an embodiment, the expandable portion is adapted to reside within an inner cavity of at least two bone fragments and provide support to the bone fragments. In an embodiment, the expandable portion is adapted to reside within an inner cavity of at least two bone fragments and secure the bone fragments in a relatively fixed relationship to each another, thus ensuring that the fractured bone can regenerate in the proper orientation and fuse the fracture.

In an embodiment, a photodynamic bone stabilization system of the present disclosure is used to treat a fracture including, but not limited to, a hand fracture, a wrist fracture, a radius fracture, an ulna fracture, a clavicle fracture, a metacarpal fracture, a phalanx fracture, a metatarsal fracture, a phalange fracture, a tibia fracture, a fibula fracture, a humerus fracture, and a rib fracture. Long bones are the large bones in the arms and legs, and include the humerus, the radius/ulna, the femur and the tibia/fibula. In an embodiment, a photodynamic bone stabilization system of the present disclosure is used to reinforce a fractured long bone. In an embodiment, a photodynamic bone stabilization system of the present disclosure is used to stabilize a fractured long bone in conjunction with anatomic reduction (i.e., proper reorientation of fractured elements to their original position, both relative to one another and relative to other adjacent anatomical features).

Figure 1:
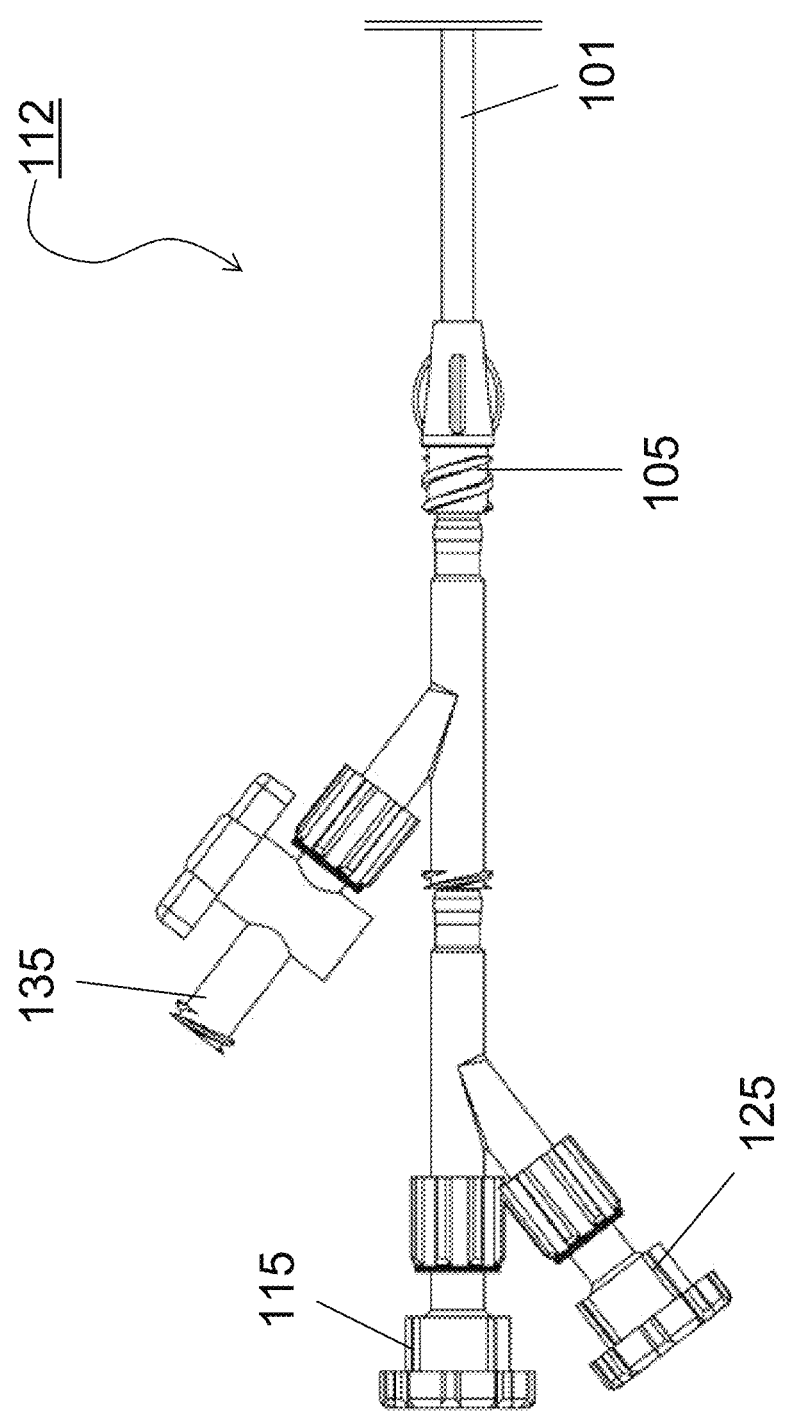
FIG. 1 shows a side view of an embodiment of a proximal end of a photodynamic bone stabilization system for repairing a weakened or fractured bone according to the present disclosure. The distal end includes an expandable portion (illustrated in an expanded position) having means for preventing shrinkage of at least a portion of the expandable portion.

FIG. 1 shows an embodiment of a proximal end 112 of a flexible insertion catheter 101 of a photodynamic bone stabilization system of the present disclosure for repairing a weakened or fractured bone. The photodynamic bone stabilization system includes a thin-walled, non-compliant, expandable portion (not visible in FIG. 1) releasably mounted at a distal end of the flexible insertion catheter 101. In an embodiment, the flexible insertion catheter 101 includes one or more radiopaque markers or bands positioned at various locations. The one or more radiopaque bands, using radiopaque materials such as barium sulfate, tantalum, or other materials known to increase radiopacity, allows a medical professional to view the insertion catheter 101 using fluoroscopy techniques. A proximal end adapter 105 includes at least one arm and at least one adapter which can be utilized for the infusion and withdrawal of fluids or as conduits for the introduction of devices (e.g., a light-conducting fiber). In an embodiment, an adapter is a Luer lock. In an embodiment, an adapter is a Tuohy-Borst connector. In an embodiment, an adapter is a multi-functional adapter. FIG. 1 shows a side view of a three arm proximal end fitting having three adapters 115, 125, and 135. Adapter 115 can accept, for example, a light-conducting fiber. Adapter 125 can accept, for example, air or fluid. In an embodiment, adapter 125 can accept, for example, a cooling medium. In an embodiment, adapter 125 can accept, for example, pressurizing medium. Adapter 135 can accept, for example, a syringe housing a light-sensitive liquid. In an embodiment, the light-sensitive liquid is a liquid monomer comprising an initiator, wherein the initiator is activated when the light-conducting fiber transmits light energy. In an embodiment, the viscosity of the light-sensitive liquid is about 1000 cP or less. In an embodiment, the light-sensitive liquid has a viscosity ranging from about 650 cP to about 450 cP. Low viscosity allows filling of the expandable portion through a very small delivery system.

In an embodiment, a syringe housing light-sensitive liquid is attached to the adapter 135 at the proximal end 112 of the insertion catheter 101, and during use of the photodynamic bone stabilization system, the syringe plunger is pushed, allowing the syringe to expel the light-sensitive liquid into an inner void 110 (not visible in FIG. 1) of the photodynamic bone stabilization system. As the light-sensitive liquid is expelled through the inner void, it reaches the expandable portion to move the expandable portion from a deflated state to an inflated state. The light-sensitive liquid can be aspirated and reinfused as necessary, allowing for adjustments to the expandable portion prior to curing of the light-sensitive liquid, wherein curing of the light-sensitive liquid hardens the expandable portion in a desired position to stabilize the fracture. These properties allow a user to achieve maximum fracture reduction prior to activating a light source and converting the liquid monomer into a hard polymer.

In an embodiment, a light-conducting fiber communicating light from a light source is introduced into adapter 115 at the proximal end 112 of the insertion catheter 101 to pass the light-conducting fiber within an inner lumen 120 (not visible in FIG. 1) of the photodynamic bone stabilization system. In an embodiment, the light-conducting fiber is an optical fiber. Optical fibers may be used in accordance with the present disclosure to communicate light from the light source to the remote location. Optical fibers use a construction of concentric layers for optical and mechanical advantages. The most basic function of a fiber is to guide light, i.e., to keep light concentrated over longer propagation distances—despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding is usually protected with at least a polymer coating. Light is kept in the "core" of the optical fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face. In some embodiments of the present disclosure, at least a portion of a length of an optical fiber is modified, e.g., by removing the cladding, in order to alter the direction, propagation, amount, intensity, angle of incidence, uniformity and/or distribution of light.

The optical fiber can be made from any material, such as glass, silicon, silica glass, quartz, sapphire, plastic, combinations of materials, or any other material, and may have any diameter, as not all embodiments of the present disclosure are intended to be limited in this respect. In an embodiment, the optical fiber is made from a polymethyl methacrylate core with a transparent polymer cladding. The optical fiber can have a diameter between approximately 0.75 mm and approximately 2.0 mm. In some embodiments, the optical fiber can have a diameter of about 0.75 mm, about 1 mm, about 1.5 mm, about 2 mm, less than about 0.75 mm or greater than about 2 mm as not all embodiments of the present disclosure are intended to be limited in this respect. In an embodiment, the optical fiber is made from a polymethyl methacrylate core with a transparent polymer cladding. It should be appreciated that the above-described characteristics and properties of the optical fibers are exemplary and not all embodiments of the present disclosure are intended to be limited in these respects. Light energy from a visible emitting light source can be transmitted by the optical fiber. In an embodiment, visible light having a wavelength spectrum of between about 380 nm to about 780 nm, between about 400 nm to about 600 nm, between about 420 nm to about 500 nm, between about 430 nm to about 440 nm, is used to cure the light-sensitive liquid.

The light-sensitive liquid remains a liquid monomer until activated by the light-conducting fiber (cures on demand). Radiant energy from the light-conducting fiber is absorbed and converted to chemical energy to quickly polymerize the monomer. This cure affixes the expandable portion in an expanded shape. A cure may refer to any chemical, physical, and/or mechanical transformation that allows a composition to progress from a form (e.g., flowable form) that allows it to be delivered through the inner void in the insertion catheter 101, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

The presently disclosed embodiments provide expandable portions of photodynamic bone stabilization systems of the present disclosure. It should be understood that any of the expandable portions disclosed herein may include one or more radiopaque markers or bands. For example, a radiopaque ink bead may be placed at a distal end of the expandable portion for alignment of the system during fluoroscopy. The one or more radiopaque bands and radiopaque ink bead, using radiopaque materials such as barium sulfate, tantalum, or other materials known to increase radiopacity, allows a medical professional to view the expandable portion during positioning to properly position the expandable during a repair procedure, and allows the medical professional to view the expandable portion during inflation and/or deflation to properly stabilize and align the fractured bones. In an embodiment, the one or more radiopaque bands permit visualization of any voids that may be created by air that gets entrapped in the expandable portion. In an embodiment, the one or more radiopaque bands permit visualization to preclude the expandable portion from misengaging or not meeting a bone due to improper inflation to maintain a uniform expandable/bone interface.

It should be understood that any of the expandable portions disclosed herein may be round, flat, cylindrical, oval, rectangular or any desired shape for a given application. The expandable portion may be formed of a pliable, resilient, conformable, and strong material, including but not limited to urethane, polyethylene terephthalate (PET), nylon elastomer and other similar polymers. In an embodiment, the expandable portion is constructed out of a PET nylon aramet or other non-consumable materials. In an embodiment, the expandable portion may be formed from a material that allows the expandable portion to conform to obstructions or curves at the site of implantation.

It should be understood that any of the expandable portions disclosed herein by way of example, but not of limitation, can have the following dimensions: In an embodiment, the expandable portion has a diameter ranging from about 5 mm to about 20 mm. In an embodiment, the expandable portion has a length ranging from about 20 mm to about 450 mm. In an embodiment, the expandable portion has a diameter of about 5 mm and a length of about 30 mm. In an embodiment, the expandable portion has a diameter of about 5 mm and a length of about 40 mm. In an embodiment, the expandable portion has a diameter of about 6 mm and a length of about 30 mm. In an embodiment, the expandable portion has a diameter of about 6 mm and a length of about 40 mm. In an embodiment, the expandable portion has a diameter of about 6 mm and a length of about 50 mm. In an embodiment, the expandable portion has a diameter of about 7 mm and a length of about 30 mm. In an embodiment, the expandable portion has a diameter of about 7 mm and a length of about 40 mm. In an embodiment, the expandable portion has a diameter of about 7 mm and a length of about 50 mm. In an embodiment, the expandable portion has a diameter of about 14 mm and a length of about 400 mm. In an embodiment, the expandable portion has a diameter of about 14 mm and a length of about 300 mm.

It should be understood that any of the expandable portions disclosed herein includes an outer surface that, in an embodiment, may be coated with materials or additives such as drugs, bone glue, proteins, growth factors, or other natural or synthetic coatings (for example, radiopaque or ultrasonically active materials). For example, after a minimally invasive surgical procedure an infection may develop in a patient, requiring the patient to undergo antibiotic treatment. An antibiotic drug may be added to the outer surface of the expandable portion to prevent or combat a possible infection. Proteins, such as, for example, bone morphogenic protein or other growth factors have been shown to induce the formation of cartilage and bone. A growth factor may be added to the outer surface of the expandable portion to help induce the formation of new bone. Due to the lack of thermal egress of the light-sensitive liquid in the expandable portion, the effectiveness and stability of the coating is maintained.

It should be understood that the expandable portions disclosed herein typically do not have any valves. One benefit of having no valves is that the expandable portion may be inflated or deflated as much as necessary to assist in the fracture reduction and placement. Another benefit of the expandable portion having no valves is the efficacy and safety of the system. Since there is no communication passage of light-sensitive liquid to the body there cannot be any leakage of liquid because all the liquid is contained within the expandable portion. In an embodiment, a permanent seal is created between the expandable portion that is both hardened and affixed prior to the insertion catheter being removed. The expandable portion may have valves, as all of the embodiments are not intended to be limited in this manner.

It should be understood that the expandable portions disclosed herein include an outer surface that is resilient and puncture resistant. In an embodiment, the outer surface of the expandable portion is substantially even and smooth. In an embodiment, the outer surface of the expandable portion is not entirely smooth and may have some small bumps or convexity/concavity along the length. In an embodiment, the outer surface of the expandable portion may have ribs, ridges, bumps or other shapes. In an embodiment, the expandable portion has a textured surface which provides one or more ridges that allow grabbing. In an embodiment, abrasively treating the outer surface of the expandable portion via chemical etching or air propelled abrasive media improves the connection and adhesion between the outer surface of the expandable portion and the bone. The surfacing significantly increases the amount of surface area that comes in contact with the bone resulting in a stronger grip.

Figure 2:
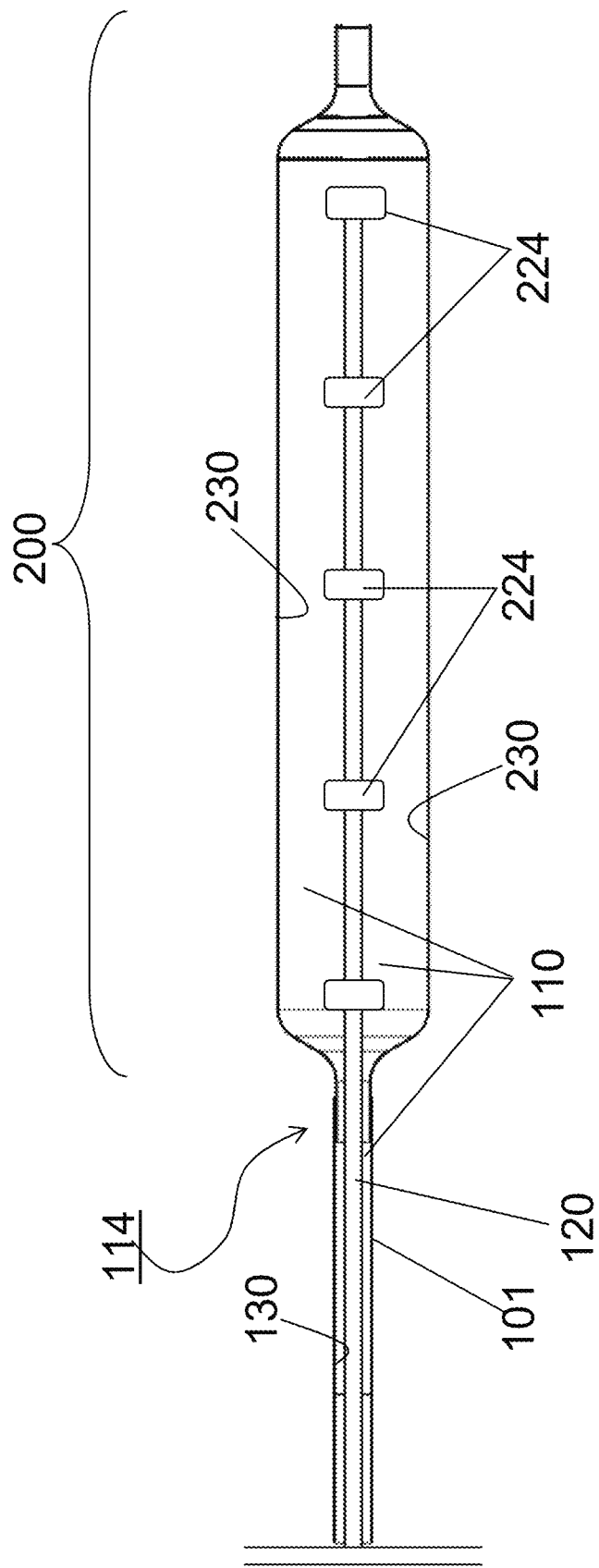
FIG. 2 shows a side view of an embodiment of a distal end of a photodynamic bone stabilization system for repairing a weakened or fractured long bone according to the present disclosure.

One possible side effect of curing a light-sensitive liquid is polymerization shrinkage. The presently disclosed embodiments provide photodynamic bone stabilization systems sufficiently designed to control polymerization shrinkage that may occur in an expandable portion of the system during use. FIG. 2 shows a side view of an embodiment of a distal end 114 of the insertion catheter 101 of FIG. 1 of a photodynamic bone stabilization system of the present sufficiently designed to control polymerization shrinkage during use. The photodynamic bone stabilization system includes the flexible insertion catheter 101; an expandable portion 200 releasably engaging the distal end 114 of the insertion catheter 101, the expandable portion 200 sufficiently designed to move from a deflated state to an inflated state; and at least two ports located at the proximal end 112 of the insertion catheter 101, the ports sufficiently designed to attach with various co-components of the photodynamic bone stabilization system, including, but not limited to, a container or syringe for delivering a light-sensitive liquid through the insertion catheter 101 and up into the expandable portion 200, a light-conducting fiber for delivering light energy to expandable portion 200, and a syringe or hose for delivering air or other fluids to the expandable portion 200 to substantially prevent polymerization shrinkage.

The inner lumen 120 passes through the longitudinal axis of the flexible insertion catheter 101 and the expandable portion 200. The inner lumen 120 is sufficiently designed to pass a light-conducting fiber. The inner void 110 exists between an outer surface of the inner lumen 120 and an inner surface 130 of the insertion catheter 101; and an outer surface of the inner lumen 120 and an inner surface 230 of the expandable portion 200 and provides a passageway for light-sensitive liquid to travel.

During a procedure for repairing a weakened to fractured long bone, the expandable portion 200 is positioned between bone fragments and light-sensitive liquid is passed through the inner void 110 of the photodynamic bone stabilization system until it reaches the expandable portion 200 and begins to expand or inflate the expandable portion 200. The expandable portion 200 is inflated in situ with light-sensitive liquid to stabilize and reduce the fracture, which can optionally be performed under fluoroscopy. Because the light-sensitive liquid will not cure until illumination with light from the light-conducting fiber, the expandable portion 200 can be inflated and deflated as many times as needed in situ to insure the proper stabilization and reduction of the fracture. Once proper positioning of the expandable portion 200 is determined, the light-conducting fiber is positioned in the inner lumen 120 of the photodynamic bone stabilization system and activated, to deliver output energy to the expandable portion 200 which will polymerize or cure the light-sensitive liquid. There is the potential that during in situ curing of the light-sensitive liquid, areas of the expandable portion 200 that are not in the immediate vicinity of the polymerization process may exhibit polymerization shrinkage upon cure of about 2 to about 3 percent. This may be especially relevant when the expandable portion 200 is used to reduce and stabilize a long bone, where the expandable portion 200 may have a diameter ranging from about 13 mm to about 20 mm and a length ranging from about 100 mm to about 450 mm. To prevent shrinkage from occurring, the inner lumen 120 in the expandable portion 200 can be pressurized by virtue of the infusion of either air or other fluids (e.g., saline or water) to cause internal diameter pressure against the light-sensitive liquid contained within the expandable portion 200 so that during the curing, the pressure keeps the light-sensitive liquid pressurized, and up in contact with inner walls 230 of the expandable portion 200. In some embodiments, the inner lumen 120 in the expandable portion 200 is configured to include areas 224 which are capable of expanding when pressurized with air or other fluids.

In an embodiment, the inner lumen 120 in the expandable portion 200 includes one area 224 configured to prevent the effects of polymerization shrinkage during curing of the light-sensitive liquid. In an embodiment, the inner lumen 120 in the expandable portion 200 includes two areas 224 configured to prevent the effects of polymerization shrinkage during curing of the light-sensitive liquid. As illustrated in FIG. 2, the inner lumen 120 in the expandable portion 200 includes five areas 224 configured to prevent the effects of polymerization shrinkage during curing of the light-sensitive liquid. Depending on the length and the diameter of the expandable portion 200 used for a particular procedure, it is possible to determine how many areas 224 are required to prevent the effects of polymerization shrinkage during curing of the light-sensitive liquid.

One possible side effect of curing a light-sensitive liquid besides polymerization shrinkage is temperature rise. The temperature rise is in direct relation with the strength of polymerization light intensity. For instance, as intensity grows, so does the temperature. The presently disclosed embodiments provide photodynamic bone stabilization systems sufficiently designed to control temperature rise that may occur in an expandable portion of the system during use. In an embodiment, the photodynamic bone stabilization systems include an expandable portion sufficiently designed to move from a deflated state to an inflated state when a light-sensitive liquid is delivered to the expandable portion. Once proper positioning and expansion of the expandable portion is determined, the light-sensitive liquid can be cured in situ to harden the expandable portion thus providing a rigid orthopedic stabilizer. During use, there is the potential that the in situ curing process of the light-sensitive liquid can cause one or more areas of the expandable portion to experience a temperature rise. To prevent a temperature rise from occurring, a cooling medium can be delivered so as to cool the expandable portion during the curing process. Cooling medium for use with a photodynamic bone stabilization system of the present disclosure includes, but is not limited to, gases, liquids and combinations thereof. Examples of gases include, but are not limited to, inert gases and air. Examples of liquids include, but are not limited to, water, saline, saline-ice mixtures, liquid cryogen. In an embodiment, the cooling medium is water. The cooling medium can be delivered to the expandable portion at room temperature or at a cooled temperature. In an embodiment, the cooling medium improves the numerical aperture between that of the light-conducting fiber and the inner lumen for the light-conducting fiber because it is desirable to take up the air between the light-conducting fiber and the material of the expandable portion so as to improve light transmission. Therefore, the light transmission will be light-conducting fiber—cooling media—expandable portion—light-sensitive liquid as opposed to light-conducting fiber—air—expandable portion—light-sensitive liquid. In an embodiment, the cooling medium transmitted through the inner lumen takes away extraneous heat.

Figure 3:
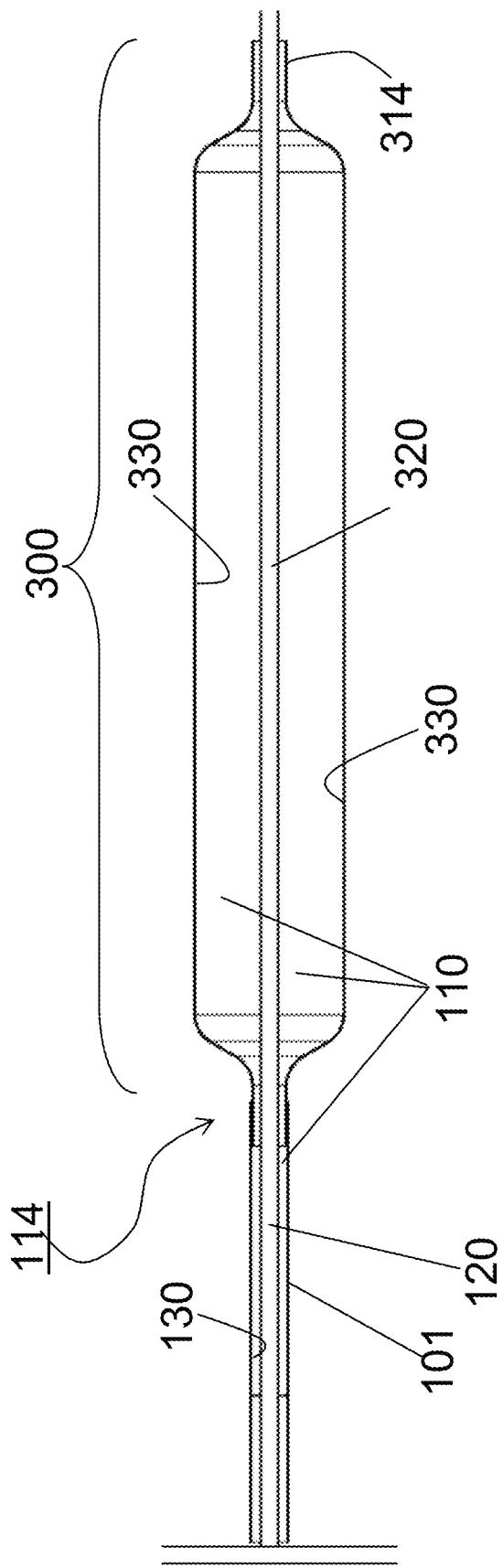
FIG. 3 shows a side view of an embodiment of a distal end of a photodynamic bone stabilization system for repairing a weakened or fractured bone according to the present disclosure. The distal end includes an expandable portion (illustrated in an expanded position) having an internal lumen penetrating through a distal end of the expandable portion for cooling through the length of the expandable portion.

FIG. 3 shows a side view of an embodiment of a distal end 114 of the insertion catheter 101 of FIG. 1 of a photodynamic bone stabilization system of the present disclosure sufficiently designed to control temperature rise during use. The photodynamic bone stabilization system includes the flexible insertion catheter 101; an expandable portion 300 releasably engaging the distal end 114 of the insertion catheter 101, the expandable portion 300 sufficiently designed to move from a deflated state to an inflated state; and at least two ports located at the proximal end 112 of the insertion catheter 101, the ports sufficiently designed to attach with various co-components of the photodynamic bone stabilization system, including, but not limited to, a container or syringe for delivering a light-sensitive liquid through the insertion catheter 101 and up into the expandable portion 300, a light-conducting fiber for delivering light energy to expandable portion 300, and a syringe or hose for delivering cooling medium to the expandable portion 300.

In the embodiment illustrated in FIG. 3, the inner lumen 120 passes through the longitudinal axis of the flexible insertion catheter 101 and through a distal end 314 of the expandable portion 300. The inner lumen 120 is sufficiently designed to pass a light-conducting fiber, and is configured to pass a cooling medium. The inner void 110 exists between an outer surface of the inner lumen 120 and an inner surface 130 of the insertion catheter 101; and an outer surface of the inner lumen 120 and an inner surface 330 of the expandable portion 300 and provides a passageway for light-sensitive liquid to travel.

During a procedure for repairing a weakened to fractured long bone, the expandable portion 300 is positioned between bone fragments and light-sensitive liquid is passed through the inner void 110 of the photodynamic bone stabilization system until it reaches the expandable portion 300 and begins to expand or inflate the expandable portion 300. The expandable portion 300 is inflated in situ with light-sensitive liquid to stabilize and reduce the fracture, which can optionally be performed under fluoroscopy. Because the light-sensitive liquid will not cure until illumination with light from the light-conducting fiber, the expandable portion 300 can be inflated and deflated as many times as needed in situ to insure the proper stabilization and reduction of the fracture. Once proper positioning of the expandable portion 300 is determined, the light-conducting fiber is positioned in the inner lumen 120 of the photodynamic bone stabilization system and activated, to deliver output energy to the expandable portion 300 which will polymerize or cure the light-sensitive liquid. During use, there is the potential that the in situ curing process of the light-sensitive liquid can cause one or more areas of the expandable portion 300 to experience a temperature rise. To prevent a temperature rise from occurring, a cooling medium can be delivered through the inner lumen 120 concurrently with the light-conducting fiber, so as to cool the expandable portion 300 during the curing process.

Figure 4:
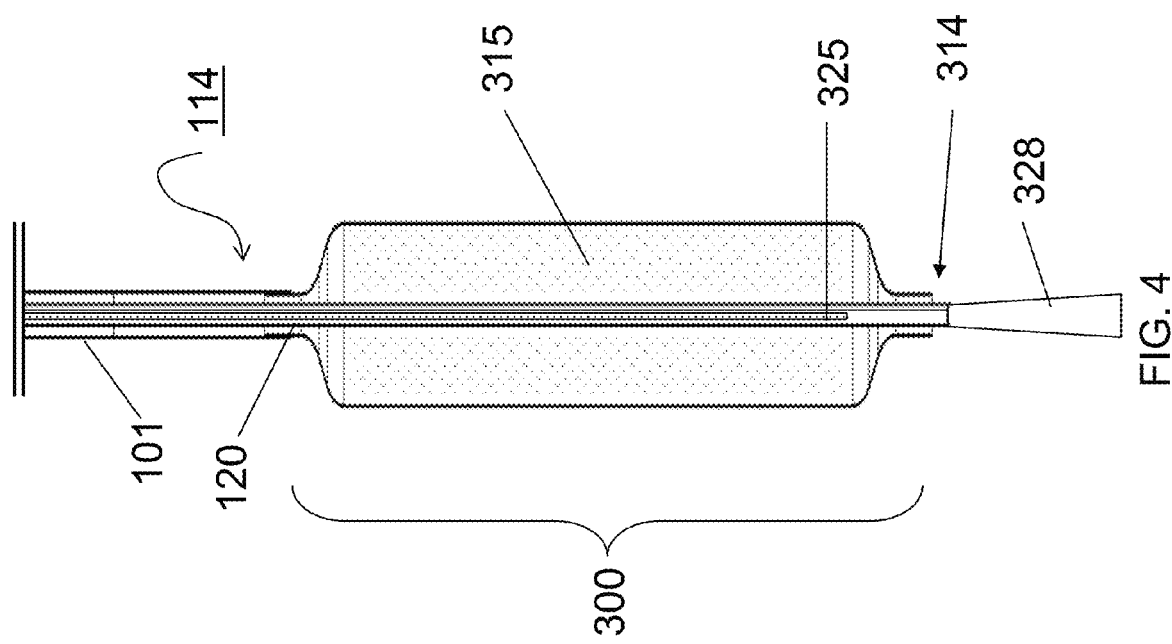
FIG. 4 shows a side view of the expandable portion of FIG. 3 after a light-sensitive liquid has been added to the expandable portion and a curing process has been initiated. A light-conducting fiber introduced into the inner lumen of the expandable portion is activated, while a cooling medium flows through the inner lumen and out the distal end of the expandable portion.

FIG. 4 shows a side view of the expandable portion 300 of FIG. 3 after a light-sensitive liquid 315 has been added to the expandable portion 300. A light-conducting fiber 325 is introduced into the inner lumen 120 of the expandable portion 300 and activated to cure the light-sensitive liquid, while a cooling medium 328 flows through the inner lumen 120 and out the distal end 314 of the expandable portion 300.

Figure 5:
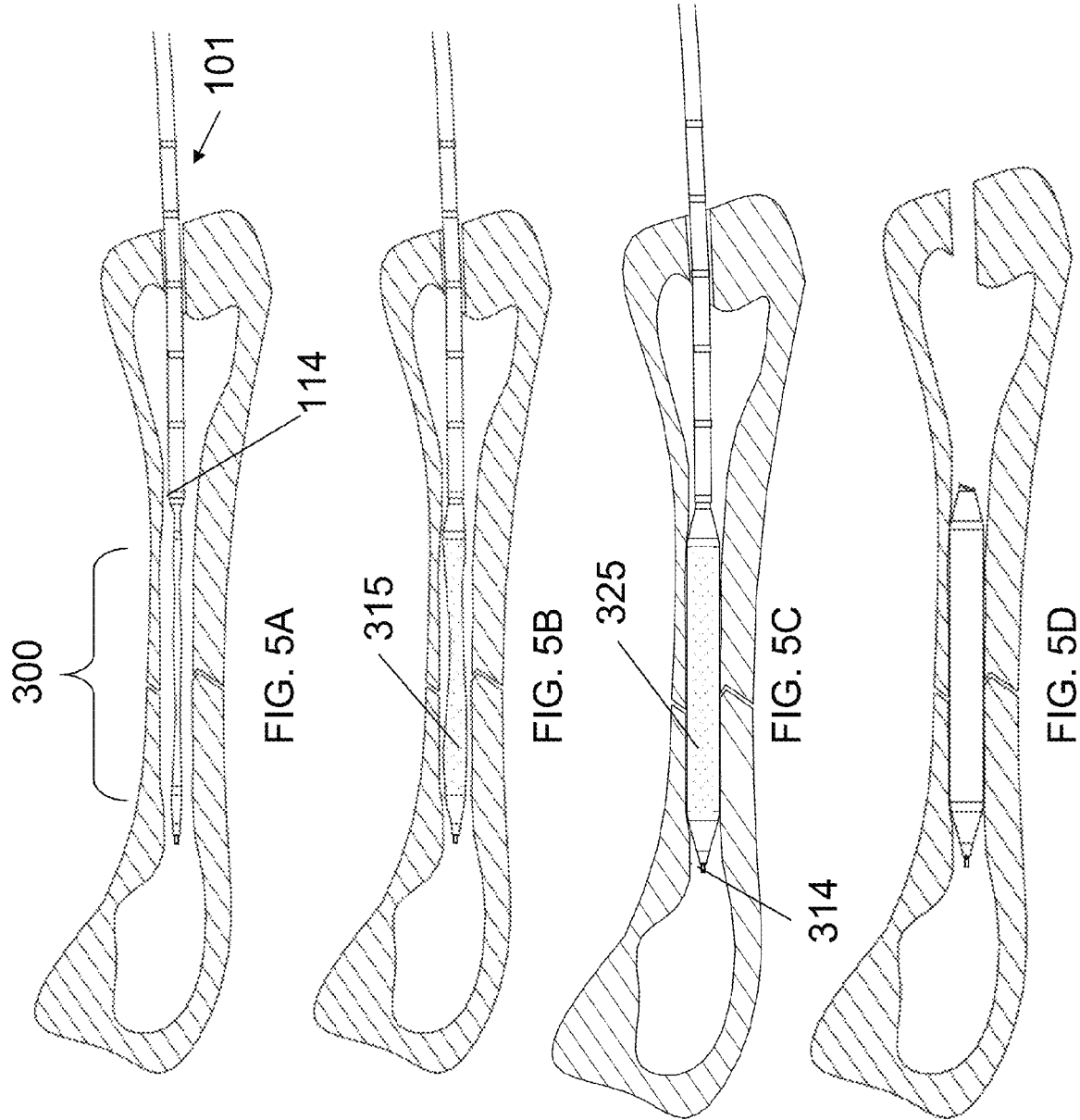
FIGS. 5A-5D illustrate an embodiment of a procedure for repairing a weakened or fractured bone.

FIGS. 5A-5D illustrate an embodiment of a procedure for repairing a weakened or fractured bone using the photodynamic bone stabilization system illustrated in FIG. 3. As illustrated in FIG. 5A, a procedure for repairing a weakened or fractured bone includes positioning the expandable portion 300 between bone fragments. In an embodiment, the expandable portion 300 spans multiple bone fragments. Once the expandable portion 300 is positioned, light-sensitive liquid monomer 315 is passed through the inner void 110 of the photodynamic bone stabilization system until it reaches the expandable portion 300 and begins to expand or inflate the expandable portion 300, as shown in FIG. 5B. The expandable portion 300 is inflated in situ with light-sensitive liquid monomer 315 to stabilize and reduce the fracture, which can optionally be performed under fluoroscopy. Because the light-sensitive liquid monomer 315 will not cure until illumination with light from the light-conducting fiber 325, the expandable portion 300 can be inflated and deflated as needed in situ to insure the proper stabilization and reduction of the fracture. Once proper positioning of the expandable portion 300 is determined, the light-conducting fiber 325 is introduced into the inner lumen 120 of the expandable portion 300 and activated, to deliver output energy to the expandable portion 300 which will polymerize or cure the light-sensitive liquid monomer, as shown in FIG. 5C. During use, there is the potential that the in situ curing process of the light-sensitive liquid monomer 315 can cause one or more areas of the expandable portion 300 to experience a temperature rise. As illustrated in FIG. 5C, to prevent a temperature rise from occurring, a cooling medium can be delivered through the lumen 120 of the expandable portion 300 to cool the expandable portion 300 during the curing process. In an embodiment, the cooling medium exits out the distal end 314 of the expandable portion 300 and collects or accumulates within the bone after exiting the expandable portion 300. FIG. 5D shows the hardened expandable portion 300 positioned within the weakened or fractured bone after the catheter 101 has been released.

Figure 6:
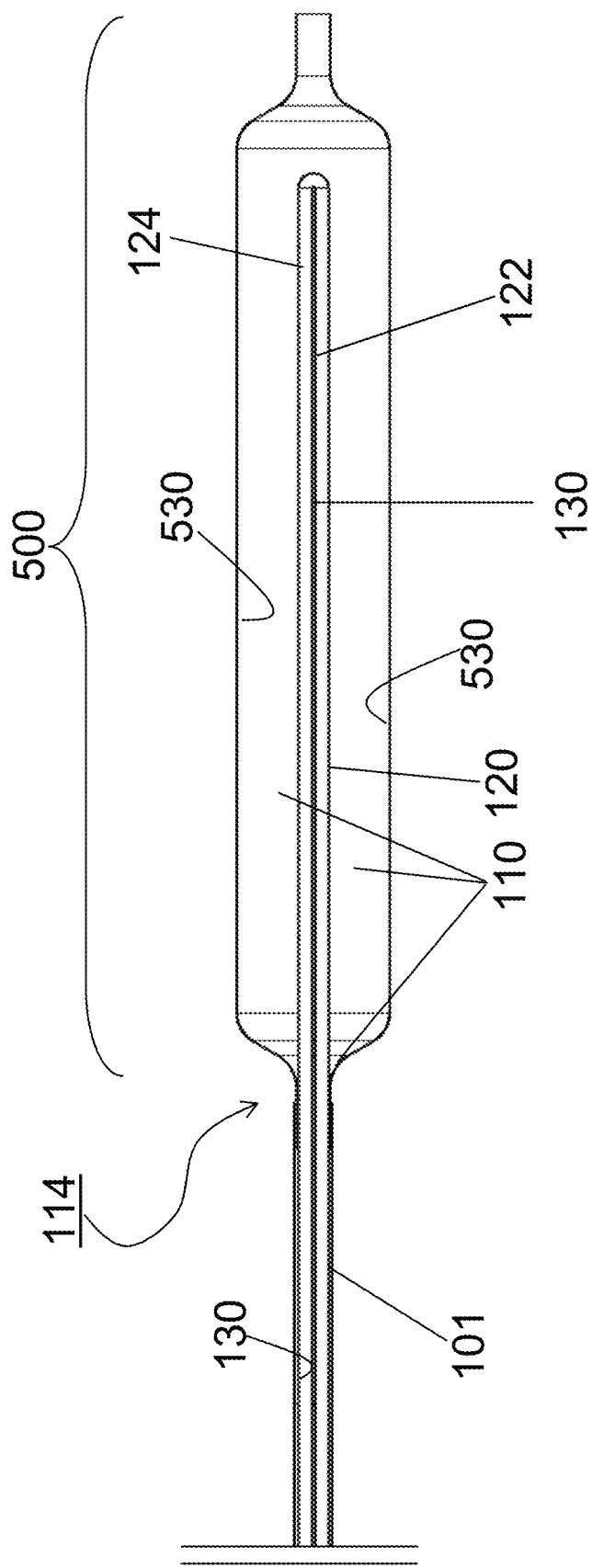
FIG. 6 shows a side view of an embodiment of a distal end of a photodynamic bone stabilization system for repairing a weakened or fractured bone according to the present disclosure. The distal end includes an expandable portion (illustrated in an expanded position) having an internal lumen with a return flow path for cooling.

FIG. 6 shows a side view of an embodiment of a distal end 114 of the insertion catheter 101 of FIG. 1 of a photodynamic bone stabilization system of the present disclosure sufficiently designed to control temperature rise during use. The photodynamic bone stabilization system includes the flexible insertion catheter 101; an expandable portion 500 releasably engaging the distal end 114 of the insertion catheter 101, the expandable portion 500 sufficiently designed to move from a deflated state to an inflated state; and at least two ports located at the proximal end 112 of the insertion catheter 101, the ports sufficiently designed to attach with various co-components of the photodynamic bone stabilization system, including, but not limited to, a container or syringe for delivering a light-sensitive liquid through the insertion catheter 101 and up into the expandable portion 500, a light-conducting fiber for delivering light energy to expandable portion 500, and a syringe or hose for delivering cooling medium to the expandable portion 300.

In the embodiment illustrated in FIG. 6, the inner lumen 120 passes through the longitudinal axis of the flexible insertion catheter 101 into the expandable portion 500. In an embodiment, the inner lumen 120 comprises a septum lumen 130 for passing the light-conducting fiber, the septum lumen 130 sufficiently designed to divide the inner lumen 120 into a cooling medium intake lumen 122 communicating with a cooling inlet and a cooling medium return lumen 124 communicating with a cooling outlet. In an embodiment, the inner lumen 120 is a return flow path for the cooling medium. The inner void 110 exists between an outer surface of the inner lumen 120 and an inner surface 530 of the insertion catheter 101; and an outer surface of the inner lumen 120 and an inner surface 530 of the expandable portion 500 and provides a passageway for light-sensitive liquid to travel.

During a procedure for repairing a weakened or fractured long bone, the expandable portion 500 is positioned between bone fragments and light-sensitive liquid is passed through the inner void 110 of the photodynamic bone stabilization system until it reaches the expandable portion 500 and begins to expand or inflate the expandable portion 500. The expandable portion 500 is inflated in situ with light-sensitive liquid to stabilize and reduce the fracture, which can optionally be performed under fluoroscopy. Because the light-sensitive liquid will not cure until illumination with light from the light-conducting fiber, the expandable portion 500 can be inflated and deflated as many times as needed in situ to insure the proper stabilization and reduction of the fracture. Once proper positioning of the expandable portion 500 is determined, the light-conducting fiber is positioned in the septum lumen 130 of the photodynamic bone stabilization system and activated, to deliver output energy to the expandable portion 500 which will polymerize or cure the light-sensitive liquid. During use, there is the potential that the in situ curing process of the light-sensitive liquid can cause one or more areas of the expandable portion 500 to experience a temperature rise. To prevent a temperature rise from occurring, a cooling medium can be delivered through the cooling medium intake lumen 122 so as to cool the expandable portion 500 during the curing process. The cooling medium is removed from the photodynamic bone stabilization system via the cooling medium return lumen 124.

Figure 7:
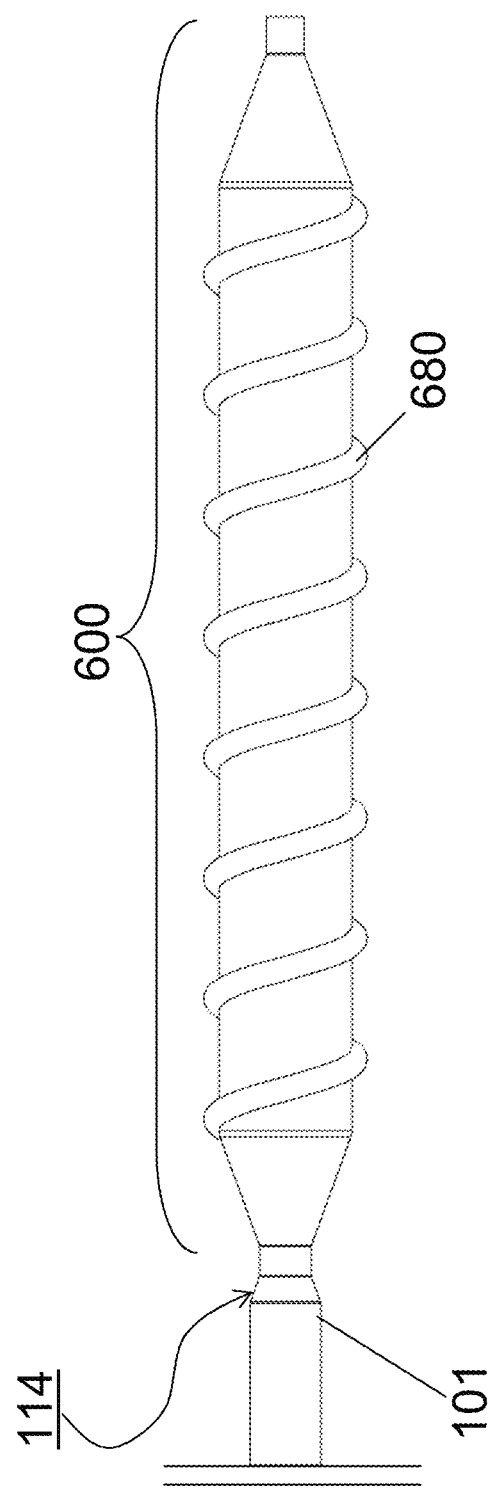
FIG. 7 shows a side view of an embodiment of a distal end of a photodynamic bone stabilization system for repairing a weakened or fractured bone according to the present disclosure. The distal end includes an expandable portion (illustrated in an expanded position) having an external helical design tubing for providing cooling medium to the expandable portion.

FIG. 7 shows a side view of an embodiment of a distal end 114 of the insertion catheter 101 of FIG. 1 of a photodynamic bone stabilization system of the present disclosure sufficiently designed to control temperature rise during use. The photodynamic bone stabilization system includes the flexible insertion catheter 101; an expandable portion 600 releasably engaging the distal end 114 of the insertion catheter 101, the expandable portion 600 sufficiently designed to move from a deflated state to an inflated state; and at least two ports located at the proximal end 112 of the insertion catheter 101, the ports sufficiently designed to attach with various co-components of the photodynamic bone stabilization system, including, but not limited to, a container or syringe for delivering a light-sensitive liquid through the insertion catheter 101 and up into the expandable portion 600, a light-conducting fiber for delivering light energy to expandable portion 600, and a syringe or hose for delivering cooling medium to the expandable portion 600.

In the embodiment illustrated in FIG. 7, the inner lumen 120 (not visible in FIG. 7) passes through the longitudinal axis of the flexible insertion catheter 101 and into the expandable portion 600. The inner lumen 120 is sufficiently designed to pass a light-conducting fiber. The inner void 110 (not visible in FIG. 7) exists between an outer surface of the inner lumen 120 and an inner surface 130 (not visible in FIG. 7) of the insertion catheter 101; and an outer surface of the inner lumen 120 and an inner surface 630 (not visible in FIG. 7) of the expandable portion 600 and provides a passageway for light-sensitive liquid to travel. The expandable portion 600 includes external helical tubing 680 for providing cooling medium to the expandable portion 600.

During a procedure for repairing a weakened to fractured long bone, the expandable portion 600 is positioned between bone fragments and light-sensitive liquid is passed through the inner void 110 of the photodynamic bone stabilization system until it reaches the expandable portion 600 and begins to expand or inflate the expandable portion 600. The expandable portion 600 is inflated in situ with light-sensitive liquid to stabilize and reduce the fracture, which can optionally be performed under fluoroscopy. Because the light-sensitive liquid will not cure until illumination with light from the light-conducting fiber, the expandable portion 600 can be inflated and deflated as many times as needed in situ to insure the proper stabilization and reduction of the fracture. Once proper positioning of the expandable portion 600 is determined, the light-conducting fiber is positioned in the inner lumen 120 of the photodynamic bone stabilization system and activated, to deliver output energy to the expandable portion 600 which will polymerize or cure the light-sensitive liquid. During use, there is the potential that the in situ curing process of the light-sensitive liquid can cause one or more areas of the expandable portion 600 to experience a temperature rise. To prevent a temperature rise from occurring, a cooling medium can be delivered through the external helical tubing 680 so as to cool the expandable portion 600 from the outside during the curing process.

In an embodiment, a method for repairing a fractured bone in a patient using a photodynamic bone stabilization system sufficiently designed to control temperature rise that may occur during use includes: a minimally invasive incision is made through a skin of the patient to expose the fractured bone. The incision may be made at the proximal end or the distal end of the fractured bone to expose a bone surface. Once the bone surface is exposed, it may be necessary to retract some muscles and tissues that may be in view of the fractured bone. At least a first proximal access hole is formed in the fractured bone by drilling or other methods known in the art. The first proximal access hole extends through a hard compact outer layer of the fractured bone into the relatively porous inner or cancellous tissue. For bones with marrow, the medullary material should be cleared from the medullary cavity prior to insertion of the insertion catheter. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. In an embodiment, such as when the expandable portion 300 of FIG. 3 is used, a second distal access hole is formed in the fractured bone. The second distal access hole is created such that the cooling medium pooling out of the distal end 314 of the expandable portion 300 can be collected. An introducer sheath may be introduced into the bone via the first access hole and placed between bone fragments of the bone to cross the location of a fracture. The introducer sheath may be delivered into the lumen of the bone and crosses the location of the break so that the introducer sheath spans multiple sections of bone fragments. The expandable portion of the insertion catheter, is delivered through the introducer sheath to the site of the fracture and spans the bone fragments of the bone. Once the expandable portion is in place, the guidewire may be removed. The location of the expandable portion may be determined using at least one radiopaque marker which is detectable from the outside or the inside of the bone. Once the expandable portion is in the correct position within the fractured bone, the introducer sheath may be removed. A delivery system housing a light-sensitive liquid is attached to the proximal end of the insertion catheter. The light-sensitive liquid is then infused through an inner void in the insertion catheter and enters the expandable portion. This addition of the light-sensitive liquid within the expandable portion causes the expandable portion to expand. As the expandable portion is expanded, the fracture is reduced.

Once orientation of the bone fragments are confirmed to be in a desired position, the light-sensitive liquid may be cured within the expandable portion, such as by illumination with a visible emitting light source. In an embodiment, visible light having a wavelength spectrum of between about 380 nm to about 780 nm, between about 400 nm to about 600 nm, between about 420 nm to about 500 nm, between about 430 nm to about 440 nm, is used to cure the light-sensitive liquid. In an embodiment, the addition of the light causes the photoinitiator in the light-sensitive liquid, to initiate the polymerization process: monomers and oligomers join together to form a durable biocompatible crosslinked polymer. In an embodiment, the cure provides complete 360 degree radial and longitudinal support and stabilization to the fractured bone. During this curing, a syringe housing the cooling medium is attached to the proximal end of the insertion catheter and continuously delivered to the expandable portion. When the expandable portion 300 of FIG. 3 is used, the cooling medium can be collected by connecting tubing to the distal end 314 of the expandable portion 300 and collecting the cooling medium via the second distal access hole. After the light-sensitive liquid has been hardened, the light-conducting fiber can be removed from the insertion catheter. The expandable portion once hardened, may be released from the insertion catheter. The hardened expandable portion remains in the fractured bone, and the insertion catheter is removed. In an embodiment, the outer surface of the hardened expandable portion makes contact with the cortical bone.

In an embodiment, a photodynamic bone stabilization system of the present disclosure is sufficiently designed to selectively stiffen an expandable portion of the system during use. In an embodiment, a photodynamic bone stabilization system of the present disclosure includes an expandable portion having a plurality of stiffening members. In an embodiment, the plurality of stiffening members are disposed along the length of the expandable portion. In an embodiment, the plurality of stiffening members are disposed along the length of an outer surface of the expandable portion. In an embodiment, the plurality of stiffening members are disposed along the length of an inner surface of the expandable portion. The stiffening members can be secured to the expandable portion in a variety of ways. For example and not limitation, the stiffening members can be secured to an adapter, e.g., luer, hub, manifold, or a reinforcement or filler material, or support member. Alternatively, the stiffening members can be secured to the expandable portion by way of an engagement member. In this manner, an engagement member can be secured to the surface of the expandable portion such that a space or cavity is defined for engaging the stiffening members. In an embodiment, the expandable portion includes a plurality of stiffening members configured to control or vary axial flexibility along a length of the expandable portion. In an embodiment, the expandable portion includes a plurality of stiffening members that can be disposed radially and/or axially.

FIG. 8A, FIG. 8B, FIG. 9A, FIG. 9B, FIG. 10A, FIG. 10B, FIG. 11A, FIG. 11B, and FIG. 12A show various embodiments of a distal end 114 of the insertion catheter 101 of FIG. 1 of a photodynamic bone stabilization system of the present disclosure sufficiently designed to control or vary axial flexibility along a length of the expandable portion. In such embodiments, a stiffness of the expandable portion has been increased due to the presence of an external stiffening member(s) (see FIG. 8A, FIG. 8B, FIG. 9A, FIG. 9B and FIG. 12A) or an internal stiffening member(s) (see FIG. 10A, FIG. 10B, FIG. 11A and FIG. 11B). In an embodiment, the expandable portion includes internal stiffening member(s). In an embodiment, the expandable portion includes external stiffening member(s). In an embodiment, the expandable portion includes a combination of internal stiffening member(s) and external stiffening member(s). In an embodiment, external and internal stiffening member(s) can be made from metal materials such as, for example, Nitonol or metallic memory-type metal pieces. In an embodiment, the stiffening member(s) or metallic pieces may be of any size or geometric shape desirable.

In an embodiment, the stiffening members or metallic pieces may protrude or extend from the expandable portion such that the metallic pieces extend beyond the diameter of the expandable portion. In an embodiment, stiffening members or metallic pieces may be situated within the expandable portion such that the diameter of the expandable portion may be substantially maintained. In an embodiment, stiffening members or metallic pieces may be integral with the expandable portion such that the expandable portion and the stiffening members are contiguous with one another. In an embodiment, stiffening members or metallic pieces may be attached, coupled, covered, sheathed, or otherwise connected to the expandable portion. In an embodiment, the stiffening members or metallic pieces may be contiguous with one another so as to form one structure around the expandable portion. In an embodiment, the stiffening members or metallic pieces can be separate and distinct so as to form multiple structures around the expandable portion. In an embodiment, the stiffening members or metallic pieces are circumferentially connected to one another at a distal end and a proximal end forming end plates. In an embodiment, the end plates help maintain the structure of the stiffening members or metallic pieces when the expandable portion is expanded.

In an embodiment, the stiffening members or metallic pieces may alter or change their configuration under a temperature change. In an embodiment, the metallic pieces expand outwards against the bone at the site of fracture. In an embodiment, the metallic pieces can expand to increase the strength of the hardened expandable potion. In an embodiment, the metallic pieces can contract to increase the strength of the hardened expandable potion. In an embodiment, an inner surface of the metallic pieces (those surfaces that are in contact with the external circumferential surface of the expandable portion) are polished to increase internal reflection of the light from the light-conducting fiber. In an embodiment, the metallic pieces are sufficiently designed to be load-bearing shapes. In an embodiment, the metallic pieces have a low profile and can handle large loads. In an embodiment, the metallic pieces may produce a greater amount of force on a large area than a small area. In an embodiment, the metallic pieces may produce a greater amount of force in a tight or narrow space that in a shallow or open space.

As illustrated in the embodiments of FIG. 8A and FIG. 8B and FIG. 9A and FIG. 9B, metallic pieces 750 and 850, respectively, are positioned on the external circumferential surface of an expandable portion 700 and 800, respectively. The metallic pieces 750 and 850 can be aligned in a longitudinal fashion, circumferentially around the expandable portion 700 (FIG. 8A and FIG. 8B) and can be interconnected with one another via connecting means 860 such as wires (FIG. 9A and FIG. 9B). The wires 860 will help hold the longitudinal metallic pieces 850 in position. The number and placement of the wires 860 can vary depending on a desired outcome. In an embodiment, the metallic pieces expand to increase the strength of the hardened expandable potion. In an embodiment, the metallic pieces contract to increase the strength of the hardened expandable potion. In an embodiment, metallic pieces 950 are positioned on an internal circumferential surface of an expandable portion 900 (FIG. 10A and FIG. 10B).

Figure 12A:
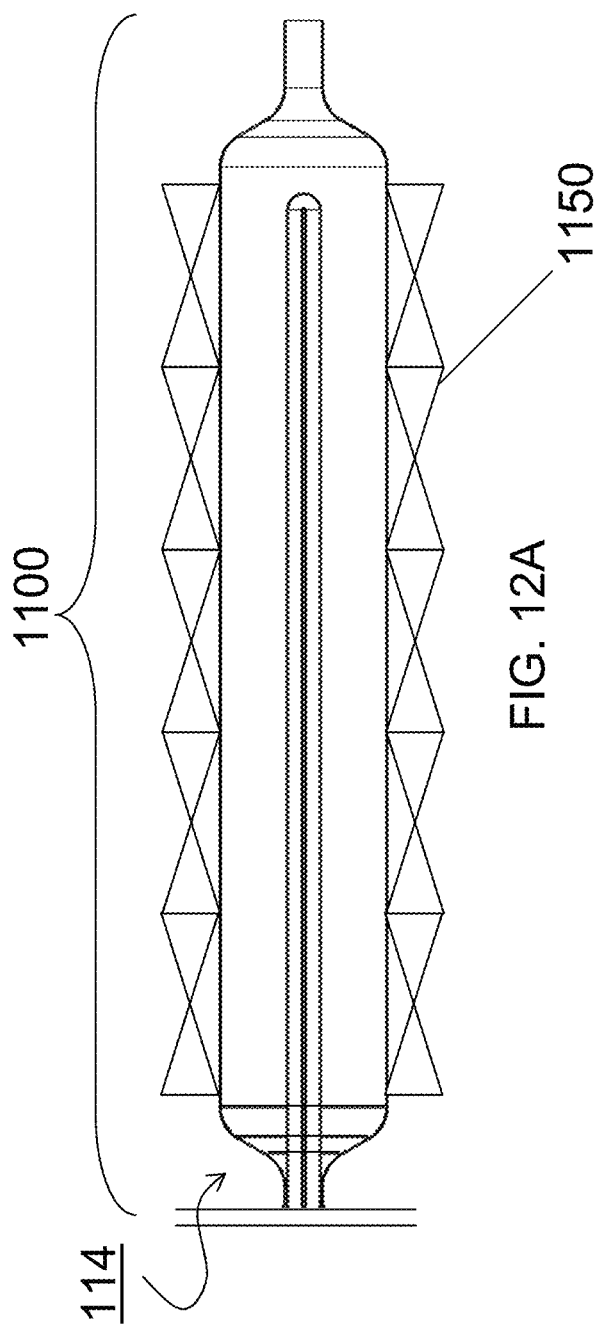
FIG. 12A shows a side view of an embodiment of a distal end of a photodynamic bone stabilization system for repairing a weakened or fractured bone according to the present disclosure. The distal end includes an expandable portion (illustrated in an expanded position) having external stiffening members that move into a corrugated shape upon a temperature change, as well as a means for cooling the expandable portion.
Figure 12G:
FIGS. 12B-12G show cross-sectional views of various embodiments of metallic memory-type metal pieces for use as external or internal stiffening members for an expandable portion of a system of the present disclosure.
Figure 12F:
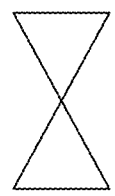
Figure 12E:
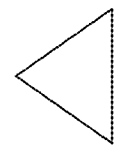
Figure 12D:
Figure 12C:
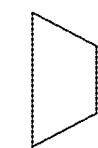
Figure 12B:

In an embodiment, two metallic memory-type metal wires 1050, such as nitonol, are positioned within the expandable portion 500 from FIG. 6 (FIG. 11A and FIG. 11B). Heat from a light-conducting fiber makes the metal wires 1050 get smaller, tensioning the hardened expandable portion 500. In an embodiment, an expandable portion 1100 is wrapped with a plurality of flat metallic plates 1150 that move into a corrugated or other shape upon a temperature change to increase the strength of the previously flat metal plate 1150 into a shape capable of handling a load (FIG. 12A). In an embodiment, the metals are rectangular, semicircular, hexagonal, or triangular in section, although not all embodiments are limited to these shapes (FIGS. 12B-12G).

The present disclosure provides photodynamic bone stabilization systems and methods for reinforcing bone. In an embodiment, a photodynamic bone stabilization system of the present disclosure is sufficiently designed to control polymerization shrinkage that may occur in an expandable portion of the system during use. In an embodiment, a photodynamic bone stabilization system of the present disclosure is sufficiently designed to control temperature rise that may occur in an expandable portion of the system during use. In an embodiment, a photodynamic bone stabilization system of the present disclosure is sufficiently designed to selectively stiffen an expandable portion of the system during use. It should be understood that the benefits provided by each of the photodynamic bone stabilization systems disclosed herein, including means to control polymerization shrinkage, means to control temperature rise, and means to selectively stiffen, can be used alone or combination. For example, in an embodiment, a photodynamic bone stabilization system of the present disclosure includes means for both controlling polymerization shrinkage and for controlling temperature rise. In an embodiment, a photodynamic bone stabilization system of the present disclosure includes means for both controlling temperature rise and means to selectively stiffen (as disclosed FIG. 11 and FIG. 12). In an embodiment, a photodynamic bone stabilization system of the present disclosure includes means for controlling polymerization shrinkage, means for controlling temperature rise, and means to selectively stiffen.

In an embodiment, a photodynamic bone stabilization system includes an insertion catheter having an elongated shaft with a proximal end, a distal end, and a longitudinal axis therebetween, the insertion catheter having an inner void for passing a light-sensitive liquid, an inner lumen for accepting a light-conducting fiber, and a pathway sufficiently designed for passing a cooling medium; an expandable portion releasably engaging the distal end of the insertion catheter, the expandable portion moving from a deflated state to an inflated state when the light-sensitive liquid is delivered to the expandable portion; and adapters releasably engaging the proximal end of the insertion catheter for receiving the light-conducting fiber, the light-sensitive liquid, and the cooling medium.

In an embodiment, a photodynamic bone stabilization system includes an insertion catheter having an elongated shaft with a proximal end, a distal end, and a longitudinal axis therebetween, the insertion catheter having an inner void for passing a light-sensitive liquid, and an inner lumen for accepting a light-conducting fiber, the inner lumen sufficiently designed to be pressurized by virtue of infusion of air, fluid, or combinations thereof; an expandable portion releasably engaging the distal end of the insertion catheter, the expandable portion moving from a deflated state to an inflated state when the light-sensitive liquid is delivered to the expandable portion; and adapters releasably engaging the proximal end of the insertion catheter for receiving the light-conducting fiber, the light-sensitive liquid, and the air or fluid, wherein the infusion of the air or fluid causes internal diameter pressure against the light-sensitive liquid contained within the expandable portion so that during a curing process, pressure keeps the light-sensitive liquid pressurized, and up in contact with inner walls of the expandable portion.

In an embodiment, a photodynamic bone stabilization system includes an insertion catheter having an elongated shaft with a proximal end, a distal end, and a longitudinal axis therebetween, the insertion catheter having an inner void for passing a light-sensitive liquid, and an inner lumen for accepting a light-conducting fiber; an expandable portion releasably engaging the distal end of the insertion catheter, the expandable portion moving from a deflated state to an inflated state when the light-sensitive liquid is delivered to the expandable portion; stiffening members engaging the expandable portion; and adapters releasably engaging the proximal end of the insertion catheter for receiving the light-conducting fiber and the light-sensitive liquid.

In an embodiment, a photodynamic bone stabilization system includes a catheter having an elongated shaft with a proximal end adapter, a distal end releasably engaging an expandable portion, and a longitudinal axis therebetween; a light-conducting fiber configured to transmit light energy to the expandable portion; a light-sensitive liquid monomer comprising an initiator, wherein the initiator is activated when the light-conducting fiber transmits the light energy to initiate polymerization of the light-sensitive liquid monomer; and a cooling medium configured to control polymerization temperature, wherein the catheter comprises an inner void sufficiently designed to pass the light-sensitive liquid monomer into the expandable portion, and wherein the catheter comprises an inner lumen sufficiently designed to pass the light-conducting fiber into the expandable portion and configured to circulate the cooling medium.

In an embodiment, a photodynamic bone stabilization system includes a light-conducting fiber configured to transmit light energy; a light-sensitive liquid monomer comprising an initiator, wherein the initiator is activated when the light-conducting fiber transmits the light energy; a pressurizing medium configured to control polymerization shrinkage; a catheter having an elongated shaft with a proximal end adapter, a distal end releasably engaging an expandable portion, and a longitudinal axis therebetween, wherein the catheter comprises an inner void and an inner lumen, wherein the inner void is sufficiently designed to pass the light-sensitive liquid monomer into the expandable portion, wherein the inner lumen is sufficiently designed to pass the light-conducting fiber into the expandable portion, and wherein the inner lumen comprises expandable portions configured to expand when the pressurizing medium is delivered to the inner lumen so as to cause internal diameter pressure against the light-sensitive liquid monomer contained within the expandable portion during polymerization.

In an embodiment, a method includes providing a system comprising a catheter having an elongated shaft with a proximal end adapter, a distal end releasably engaging an expandable portion, and a longitudinal axis therebetween; a light-conducting fiber configured to transmit light energy to the expandable portion; a light-sensitive liquid monomer comprising an initiator, wherein the initiator is activated when the light-conducting fiber transmits the light energy, to initiate polymerization of the light-sensitive liquid monomer; and a cooling medium configured to control polymerization temperature, wherein the catheter comprises an inner void sufficiently designed to pass the light-sensitive liquid monomer into the expandable portion, and wherein the catheter comprises an inner lumen sufficiently designed to pass the light-conducting fiber into the expandable portion and configured to circulate the cooling medium; inserting the expandable portion of the system into an intramedullary canal spanning a fracture site comprising a plurality of fractured pieces; infusing the light-sensitive liquid monomer into the inner void of the catheter so that the light-sensitive liquid monomer expands the expandable portion until the fractured pieces are substantially restored to their natural positions; inserting the light-conducting fiber into the inner lumen of the catheter so that the light-conducting fiber resides in the expandable portion; activating the light-conducting fiber to transmit light energy to the expandable portion to initiate in situ polymerization of the light-sensitive liquid monomer within the expandable portion; infusing the cooling medium into the inner lumen of the catheter to control polymerization temperature; and completing the in situ polymerization of the light-sensitive liquid monomer to harden the expandable portion at the fracture site.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A photodynamic bone stabilization system comprising:
a catheter having an elongated shaft with a distal end releasably engaging an expandable portion, and a longitudinal axis therebetween;
a light-conducting fiber configured to transmit light energy into the expandable portion;
a light-sensitive liquid monomer comprising an initiator within the expandable portion, wherein the initiator is activated when the light-conducting fiber transmits the light energy for polymerization of the light-sensitive liquid monomer; and
a cooling medium configured to control polymerization, wherein the catheter comprises an inner void sufficiently designed to pass the light-sensitive liquid monomer into the expandable portion, and wherein the catheter comprises an inner lumen sufficiently designed to pass the light-conducting fiber into the expandable portion and configured to circulate the cooling medium, and wherein the inner lumen in the expandable portion comprises at least two separate areas configured to expand when a pressurizing medium is delivered to the inner lumen in the expandable portion to cause internal diameter pressure against the light-sensitive liquid monomer during polymerization.

2. The system of claim 1 wherein the catheter further comprises a proximal end adapter, wherein the proximal end adapter comprises:
a first adapter for infusion of the light-sensitive liquid;
a second adapter for infusion of the cooling medium; and
a third adapter for introduction of the light-conducting fiber.

3. The system of claim 1 wherein the expandable portion is fabricated from a thin-walled, non-compliant PET nylon aramet.

4. The system of claim 1 wherein the cooling medium is one of saline or water.

5. The system of claim 1 wherein the light-conducting fiber is an optical fiber.

6. The system of claim 1 wherein at least a portion of the inner lumen in the expandable portion is expandable when pressurized with air or other fluids, the expandable portions configured to prevent effects of polymerization shrinkage during curing of the light-sensitive liquid.

7. The system of claim 1 wherein the expandable portion includes stiffening members for selectively stiffening the expandable portion.

8. The system of claim 7 wherein the stiffening members are positioned radially around an outside surface of the expandable portion.

9. The system of claim 7 wherein the stiffening members are positioned radially around an inner surface of the expandable portion.

10. The system of claim 7 wherein the stiffening members are fabricated from metallic memory-type metal pieces.

11. The system of claim 1 wherein the inner lumen passes through a distal end of the expandable portion.

12. The system of claim 1 wherein the inner lumen comprises a cooling medium intake lumen and a cooling medium return lumen.

13. A photodynamic bone stabilization system comprising:
a light-conducting fiber configured to transmit light energy;
a light-sensitive liquid monomer comprising an initiator, wherein the initiator is activated when the light-conducting fiber transmits the light energy to initiate polymerization of the light-sensitive liquid monomer;
a pressurizing medium configured to control polymerization shrinkage; and
a catheter having an elongated shaft, a distal end releasably engaging an expandable portion, and a longitudinal axis therebetween,
wherein the catheter comprises an inner void and an inner lumen,
wherein the inner void is sufficiently designed to pass the light-sensitive liquid monomer into the expandable portion,
wherein the inner lumen is sufficiently designed to pass the light-conducting fiber into the expandable portion, and
wherein the inner lumen in the expandable portion comprises at least two separate areas configured to expand when the pressurizing medium is delivered to the inner lumen in the expandable portion so as to cause internal diameter pressure against the light-sensitive liquid monomer contained within the expandable portion during polymerization.

14. The system of claim 13 further comprising:
a cooling medium configured to control polymerization temperature of the expandable portion.

15. A method comprising:
inserting an expandable portion of a photodynamic bone stabilization system into an intramedullary canal spanning a bone fracture site comprising a plurality of fractured bone pieces, wherein the photodynamic bone stabilization system comprises:
a catheter having a distal end releasably engaging the expandable portion, an inner void, and an inner lumen extending longitudinally within the catheter into the expandable portion, wherein a septum lumen divides the inner lumen into a cooling medium intake lumen and a cooling lumen return lumen;
infusing a light-sensitive liquid monomer into the inner void of the catheter so that the light-sensitive liquid monomer expands the expandable portion until the fractured pieces are substantially restored to their natural positions;
inserting a light-conducting fiber into the septum lumen of the catheter so that the light-conducting fiber resides in the expandable portion, wherein the light-conducting fiber is configured to transmit light energy to the expandable portion;
activating the light-conducting fiber to transmit light energy to the expandable portion to initiate polymerization of the light-sensitive liquid monomer within the expandable portion;
delivering a pressurizing medium to the inner lumen of the catheter;
infusing a cooling medium into the cooling medium intake lumen of the catheter to control polymerization temperature; and
completing the polymerization of the light-sensitive liquid monomer to harden the expandable portion at the bone fracture site,
wherein the inner lumen in the expandable portion comprises at least two separate areas configured to expand when the pressurizing medium is delivered to the inner lumen to cause internal diameter pressure against the light-sensitive liquid monomer contained within the expandable portion during polymerization.

16. The method of claim 15 further comprising removing the light-conducting fiber from the catheter.

17. The method of claim 15 further comprising releasing the expandable portion from the catheter.

18. The method of claim 15 wherein the hardened expandable portion stabilizes the bone fracture site.

19. The method of claim 15 wherein the hardened expandable portion maintains the positions of the plurality of fractured bone pieces while the bone heals.

20. The method of claim 15 wherein the hardened expandable portion immobilizes joints above and below the fracture site.

* * * * *